(12) United States Patent
Papsdorf

(10) Patent No.: US 12,708,567 B2
(45) Date of Patent: Aug. 18, 2026

(54) METHODS AND APPARATUSES FOR MANUFACTURING A JOINED RESEALABLE ABSORBENT ARTICLE

(71) Applicant: The Procter & Gamble Company, Cincinnati, OH (US)

(72) Inventor: Clifford Theodore Papsdorf, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 18/739,395

(22) Filed: Jun. 11, 2024

(65) Prior Publication Data

US 2025/0000713 A1 Jan. 2, 2025

Related U.S. Application Data

(60) Provisional application No. 63/523,938, filed on Jun. 29, 2023.

(51) Int. Cl.
*A61F 13/15* (2006.01)

(52) U.S. Cl.
CPC .. *A61F 13/15747* (2013.01); *A61F 13/15699* (2013.01); *A61F 13/15723* (2013.01); *A61F 13/15739* (2013.01)

(58) Field of Classification Search
CPC .......... A61F 13/15747; A61F 13/15699; A61F 13/15723; A61F 13/15739; A61F 13/15585; A61F 13/15593; A61F 13/15601; A61F 13/15609; B65H 2801/57; B31D 1/0075; B29L 2031/4878; B29L 2031/769
USPC ....... 493/369, 374; 604/385.01, 385.03, 389, 604/390, 392, 391
See application file for complete search history.

(56) References Cited

U.S. PATENT DOCUMENTS 4,209,016 A 6/1980 Schaar
5,053,028 A * 10/1991 Zoia ...................... A61F 13/581 604/389
5,108,384 A 4/1992 Goulait
(Continued)

FOREIGN PATENT DOCUMENTS

EP 0927550 A1 7/1999
EP 1600132 A1 11/2005
(Continued)

OTHER PUBLICATIONS

EPO Search Report and Opinion for Application No. 24181860.8 dated Oct. 17, 2024, 8 pages.

*Primary Examiner* — Linda J. Hodge
(74) *Attorney, Agent, or Firm* — Gregory P. Habiak; Charles Matson

(57) ABSTRACT

A method including: forming a first fold line; forming a second fold line to define a first segment of a first outer region extending between a first cut edge and the second fold line and to define a second segment extending between the first fold line and the second fold line; positioning a first surface of the first segment into a facing relationship with a first surface of the second segment; unfolding the first outer region to position the second surface of the first segment into a facing relationship with a first surface of an adjacent second outer region; and refastenably connecting the second surface of the first segment of the first outer region with the first surface of the second outer region.

21 Claims, 26 Drawing Sheets

(56) References Cited

U.S. PATENT DOCUMENTS

| | | | | |
|---|---|---|---|---|
| 5,370,634 | A | 12/1994 | Ando | |
| 5,624,428 | A | 4/1997 | Sauer | |
| 5,643,245 | A * | 7/1997 | Osborn, III | A61F 13/476 604/389 |
| 6,454,752 | B1 | 9/2002 | Huang | |
| 6,494,873 | B2 * | 12/2002 | Karlsson | A61F 13/5622 604/394 |
| 6,524,293 | B1 | 2/2003 | Elsberg et al. | |
| 2002/0165517 | A1 | 11/2002 | Datta | |
| 2002/0173768 | A1 | 11/2002 | Elsberg | |
| 2003/0088223 | A1 | 5/2003 | Vogt et al. | |
| 2003/0100880 | A1 | 5/2003 | Magee | |
| 2003/0216706 | A1 | 11/2003 | Olsson | |
| 2009/0043275 | A1 * | 2/2009 | Perneborn | A61F 13/56 156/162 |
| 2012/0152436 | A1 * | 6/2012 | Schneider | A61F 13/15747 156/66 |
| 2015/0133885 | A1 * | 5/2015 | Sheehan | A61F 13/494 604/386 |
| 2015/0173957 | A1 * | 6/2015 | Schneider | A61F 13/15756 493/374 |
| 2015/0297417 | A1 * | 10/2015 | Umebayashi | A61F 13/15804 156/227 |
| 2017/0065461 | A1 * | 3/2017 | Schneider | A61F 13/15723 |
| 2017/0252230 | A1 * | 9/2017 | Mueller | A61F 13/4963 |
| 2019/0000686 | A1 * | 1/2019 | Carlén | A61F 13/5655 |
| 2021/0145650 | A1 * | 5/2021 | Surushe | A61F 13/15699 |

FOREIGN PATENT DOCUMENTS

| | | | | |
|---|---|---|---|---|
| WO | 0236060 | A2 | 5/2002 | |
| WO | WO-2017006677 | A1 * | 1/2017 | A61F 13/15 |

* cited by examiner 140
114
114D
114U
118
102
106
122
104
128
MD
CD
Operator Side 142
CD
MD
118
102
106
104
114
114U
114D
128
Operator Side
Drive side
CP1
CP2
CP3
110
126
132
100
122
506
A 100
MD
126
120
124
134
114U
114IE
132
136
130
116
122
118
104
102
106
Operator Side View 114U
106

120
116
118
114U 134
114U
132
136
130

114U

114U 120
114U 126
110
132
114U
112
Operator Side View 106
102 118
136
114U
134
134
114D
136
102 118
106
104 120
104 120
106
106
Drive Side View
Direction of rotation 500
502
142
CD
800
600
510
504
504A
504C
CP0
CP1
CP2
CP3
CP4
CP5
520
522U
522D
562
506
508
544
542

522U
508
522D
544
542
104, 122
104, 122
540U
540D
CP3
504

104, 122
556
554
552
550
542
560
130
132
524
522D
508
562
102
116
124
544
558
Before CP1
540D 102
116
578
130
136
132
134
562
582
570D
Approximately CP2

METHODS AND APPARATUSES FOR MANUFACTURING A JOINED RESEALABLE ABSORBENT ARTICLE

CROSS REFERENCE TO RELATED APPLICATION

This application claims the benefit of U.S. Provisional Application No. 63/523,938, filed Jun. 29, 2023, which is incorporated by reference herein in its entirety.

FIELD

The present disclosure relates generally to an apparatuses and methods for manufacturing absorbent articles, and more specifically, to apparatuses and methods for forming belt overlapping hook seams in absorbent articles.

BACKGROUND

Along an assembly line, various types of articles, such as for example, diapers and other absorbent articles, may be assembled by adding components to and/or otherwise modifying an advancing continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics.

In some converting configurations, discrete absorbent chassis are arranged with a longitudinal axis parallel with a cross direction. The discrete absorbent chassis are spaced apart from each other in a machine direction and opposing waist regions of discrete absorbent chassis are then connected with continuous lengths of front and back (e.g., first and second) belt webs advancing in the machine direction, forming a continuous length of absorbent articles. The continuous length of absorbent articles may then be folded in a cross-direction CD. The continuous length of absorbent articles is then subjected to a final knife cut to separate the web(s) into discrete diapers or other absorbent articles.

Once folded the first belt may be positioned directly over and rest on the second belt. Prior to the cutting step, adjacent bonds may be created that connect the first belt and the second belt. The adjacent bonds straddle a location of the subsequent cut. Once cut, the absorbent articles are separated from each other while the first belt and the second belt of a given absorbent article are connected to each other. However, when the absorbent article is put into use, the belts undergo tension. This tension causes the ends of the first belt to pull apart from the ends of the second belt at the bond. The configuration of the bond causes a peeling action at the bond, which can stress the bond. In addition, permanent bonds like this do not allow for customized fit and easy application and removal of the absorbent article. In response, the industry has created absorbent articles with rescalable side seams instead of permanently bonded connection. However, formation of the folds necessary to create the resealable side seams may be complex and there is room in the art for improvement.

The discussion of shortcomings and needs existing in the field prior to the present disclosure is in no way an admission that such shortcomings and needs were recognized by those skilled in the art prior to the present disclosure.

SUMMARY

Various configurations solve the above-mentioned problems and provide methods and devices useful for creating absorbent articles with rescalable side seams. Rescalable side scams provide superior resistance to tensile strength in the waistband, provide improved fit by permitting adjustment of the side seams, and easy application and removal of the absorbent article. The methods and apparatuses disclosed herein provide a plug-in solution that enables formation of the proper folds necessary to create the resealable side seam within existing production lines. The apparatuses receive a continuous web, cut the continuous web into discrete absorbent articles having a first belt (e.g., a front belt) and a second belt (e.g., a rear belt), fold the ends of at least the first belt, properly dimension a length of the second belt, and secure the ends to the first belt to the ends of the second belt to form the rescalable side seams in a smooth, continuous process. The methods and apparatuses thereby represented an improvement in the art.

One general aspect includes a method of assembling absorbent articles. The method also includes advancing a substrate in a machine direction, the substrate may include a first surface and an opposing second surface, the substrate may include a first outer region separated from a second outer region in a cross direction by a central region, where the first outer region and the second outer region are continuous in the machine direction and where the central region is discontinuous in the machine direction. The method also includes folding the central region around a folding axis by about 180 degrees to position the first surface of the second outer region into a facing relationship with the first surface of the first outer region. The method also includes cutting the first outer region and the second outer region in the cross direction to define a first cut edge of the first outer region and a second cut edge of the second outer region. The method also includes forming a first fold line in the first outer region, where the first fold line extends in the cross direction. The method also includes forming a second fold line in the first outer region, where the second fold line extends in the cross direction to define a first segment of the first outer region extending between the first cut edge and the second fold line and to define a second segment extending between the first fold line and the second fold line. The method also includes positioning the first surface of the first segment into a facing relationship with the first surface of the second segment. The method also includes unfolding the first outer region along the first fold line to position the second surface of the first segment of the first outer region into a facing relationship with the first surface of the second outer region adjacent the second cut edge. The method also includes refastenably connecting the second surface of the first segment of the first outer region with the first surface of the second outer region adjacent the second cut edge. Other configurations of this aspect include corresponding computer systems, apparatus, and computer programs recorded on one or more computer storage devices, each configured to perform the actions of the methods.

One general aspect includes a method of assembling absorbent articles. The method also includes advancing a first clastic laminate in a machine direction, the first clastic laminate may include a first surface and an opposing second surface. The method also includes advancing a second elastic laminate in the machine direction, the second elastic laminate may include a first surface and an opposing second surface, the second elastic laminate separated from the first clastic laminate in a cross direction. The method also includes connecting opposing end portions of a chassis with the first surface of the first elastic laminate and the first surface of the second elastic laminate. The method also includes folding the chassis around a folding axis by about 180 degrees to position the first surface of the second clastic laminate into a facing relationship with the first surface of the first clastic laminate. The method also includes cutting the first and second clastic laminates together in the cross direction to define a first cut edge of the first clastic laminate and a second cut edge of the second clastic laminate. The method also includes forming a first fold line in the first elastic laminate, where the first fold line extends in the cross direction. The method also includes forming a second fold line in the first clastic laminate, where the second fold line extends in the cross direction to define a first segment of the first outer region extending between the first cut edge and the second fold line and to define a second segment extending between the first fold line and the second fold line. The method also includes positioning the first surface of the first segment into a facing relationship with the first surface of the second segment. The method also includes unfolding the first elastic laminate along the first fold line to position the second surface of the first segment of the first elastic laminate into a facing relationship with the first surface of the second clastic laminate adjacent the second cut edge. The method also includes refastenably connecting the second surface of the first segment of the first elastic laminate with the first surface of the second elastic laminate adjacent the second cut edge. Other configurations of this aspect include corresponding computer systems, apparatus, and computer programs recorded on one or more computer storage devices, each configured to perform the actions of the methods.

One general aspect includes an apparatus for forming a refastenable connection between a first elastic laminate and a second elastic laminate. The apparatus also includes a drum adapted to rotate about an axis, the drum may include an outer circumferential surface; a folding mechanism adjacent the outer circumferential surface, the folding mechanism may include a first folding member may include a first holding surface and a second folding member may include a second holding surface, the first folding member and the second folding member pivotally connected with the drum and pivotal between a first position and a second position, where the first holding surface and the second holding surface are generally aligned with the outer circumferential surface of the drum in the first position, and where the first holding surface and the second holding surface are retracted radially inward from the outer circumferential surface of the drum in the second position; and an anvil positioned circumferentially between the first folding member and the second folding member. Other configurations of this aspect include corresponding computer systems, apparatus, and computer programs recorded on one or more computer storage devices, each configured to perform the actions of the methods.

These and other features, aspects, and advantages of various configurations will become better understood with reference to the following description, figures, and claims.

BRIEF DESCRIPTION OF THE DRAWINGS

Many aspects of this disclosure may be better understood with reference to the following figures.

Figure 1:
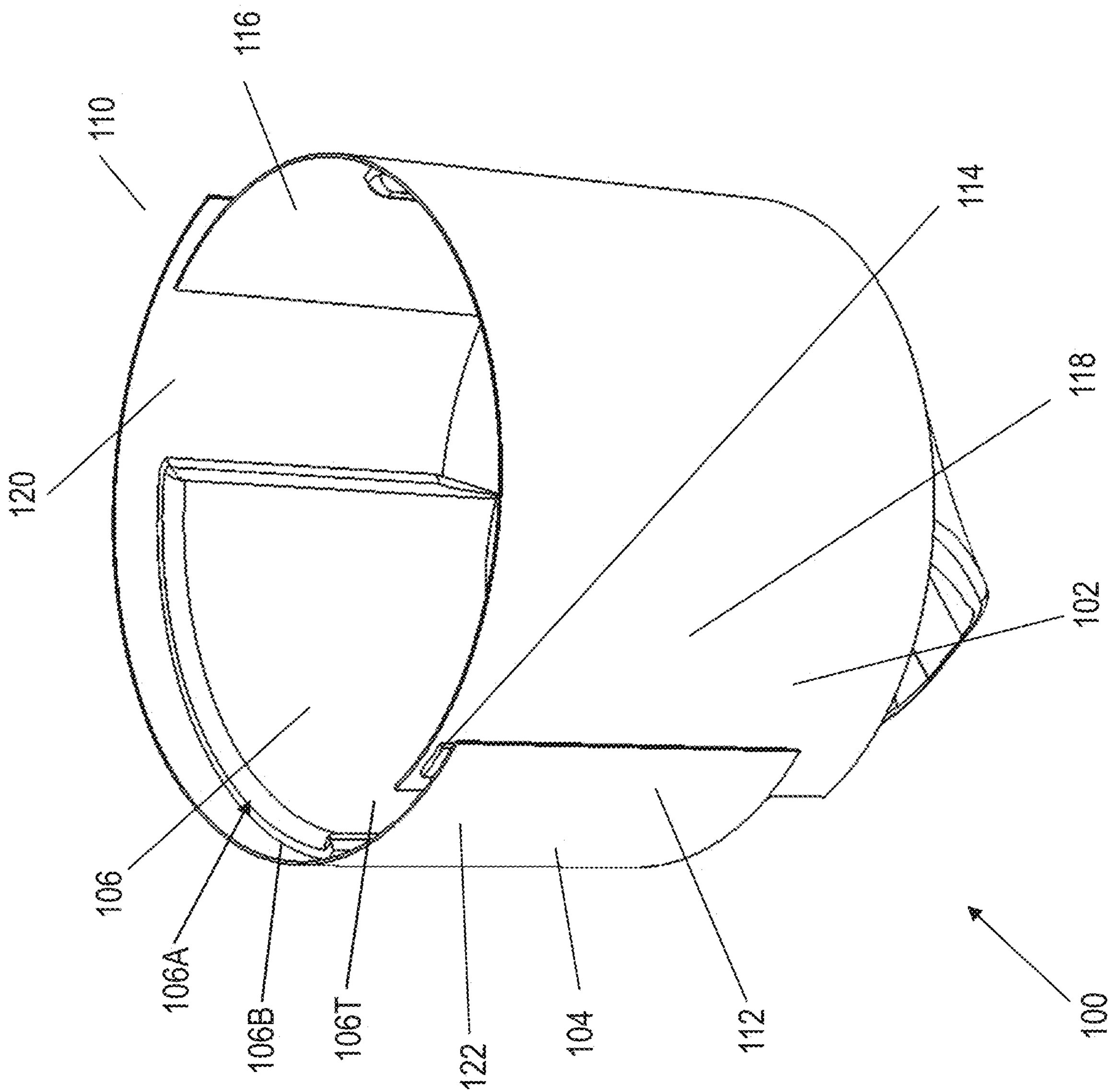
FIG. 1 is an example according to various configurations illustrating a perspective view of an absorbent article.

It should be understood that the various configurations are not limited to the examples illustrated in the figures.

DETAILED DESCRIPTION

Introduction and Definitions

This disclosure is written to describe the invention to a person having ordinary skill in the art, who will understand that this disclosure is not limited to the specific examples or configurations described. The examples and configurations are single instances of the invention which will make a much larger scope apparent to the person having ordinary skill in the art. Unless defined otherwise, all technical and scientific terms used herein have the same meaning as commonly understood by the person having ordinary skill in the art. It is also to be understood that the terminology used herein is for the purpose of describing examples and configurations only, and is not intended to be limiting, since the scope of the present disclosure will be limited only by the appended claims.

All the features disclosed in this specification (including any accompanying claims, abstract, and drawings) may be replaced by alternative features serving the same, equivalent, or similar purpose, unless expressly stated otherwise. Thus, unless expressly stated otherwise, each feature disclosed is one example only of a generic series of equivalent or similar features. The examples and configurations described herein are for illustrative purposes only and that various modifications or changes in light thereof will be suggested to the person having ordinary skill in the art and are to be included within the spirit and purview of this application. Many variations and modifications may be made to the configurations of the disclosure without departing substantially from the spirit and principles of the disclosure. All such modifications and variations are intended to be included herein within the scope of this disclosure. For example, unless otherwise indicated, the present disclosure is not limited to particular materials, reagents, reaction materials, manufacturing processes, or the like, as such can vary. It is also to be understood that the terminology used herein is for purposes of describing particular configurations only and is not intended to be limiting. It is also possible in the present disclosure that steps may be executed in different sequence where this is logically possible.

All numeric values are herein assumed to be modified by the term "about," whether or not explicitly indicated. The term "about" generally refers to a range of numbers that one of skill in the art would consider equivalent to the recited value (for example, having the same function or result). In many instances, the term "about" may include numbers that are rounded to the nearest significant figure.

In everyday usage, indefinite articles (like "a" or "an") precede countable nouns and noncountable nouns almost never take indefinite articles. It must be noted, therefore, that, as used in this specification and in the claims that follow, the singular forms "a," "an," and "the" include plural referents unless the context clearly dictates otherwise. Thus, for example, reference to "a support" includes a plurality of supports. Particularly when a single countable noun is listed as an element in a claim, this specification will generally use a phrase such as "a single." For example, "a single support."

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

In this specification and in the claims that follow, reference will be made to a number of terms that shall be defined to have the following meanings unless a contrary intention is apparent.

"Absorbent article" refers to devices that absorb and contain liquid, and more specifically, refers to devices that are placed against or in proximity to the body of the wearer to absorb and to contain various exudates discharged from the body.

"Align" or "aligned" or "aligning" means to place or to arrange in a straight line. Aligning edges of substrates, therefore, means arranging the substrates so that the edges in question extend along approximately the same line. It is to be appreciated that aligning edges of substrates may be accomplished in a variety of ways, including placing the substrates one on top of the other or side by side.

"Facing relationship" refers to a relative positioning of materials, such as substrates, in which a surface of one material is oriented toward a surface of another material. For example, when two substrates are stacked on top of each other, they are in a facing relationship. The term does not require or exclude the presence of intervening objects, materials, or layers.

"Machine direction" (MD) refers to the direction of material flow through a process. In addition, relative placement and movement of material may be described as flowing in the machine direction through a process from upstream in the process to downstream in the process.

"Cross direction" (CD) refers to a direction that is generally perpendicular to the machine direction.

Discussion of the Figures

The present inventor has developed unique and innovative methods and apparatuses for manufacturing a joined rescalable absorbent article. In various configurations, the absorbent article is a pant article, or a diaper product and the absorbent article may be disposable. It is to be appreciated that the apparatus and methods herein may be configured to produce various types of absorbent articles, such as for example, the absorbent articles disclosed in U.S. Patent Publication Nos. 2022/0401271A1 and 2022/0401272A1, which are incorporated by reference herein.

FIG. 1 is an example according to various configurations illustrating a perspective view of an absorbent article 100. The absorbent article 100 includes a first belt 102 (a.k.a. a first outer region), a second belt 104 (a.k.a. a second outer region), and a chassis 106 (a.k.a. a central region). In a configuration, the first belt 102 is composed of a first elastic laminate and the second belt 104 is composed of a second elastic laminate. The belts may be constructed by laminating continuous parallel strands of strained elastic strands between an inner and outer non-woven. Hot melt adhesive may be applied to adhere the inner and outer non-wovens with the elastic strands as they are combined. Example suitable materials for the belts include nonwovens, woven fabrics, paper, plastic films, elastic films, etc. The elastic laminate may use alternative elastic materials such as elastic films, clastic woven substrate, elastic nonwoven substrate, etc. The elastic laminate may include multiple discrete pieces of material joined together. The discrete pieces of material may have similar or differing properties, such as stiffness and elasticity. The first belt 102 and/or the second belt 104 may each be composed of one or plural elastic laminate segments joined together.

In a configuration, the chassis 106 includes a topsheet 106T, a backsheet 106B, and an absorbent assembly 106A positioned between the topsheet 106T and the backsheet 106B. The absorbent article 100 includes an overlap 110 on each side that forms respective rescalable seams 112. The rescalable seams 112 create a rescalable/re-positional/adjustable waist circumference for the absorbent article 100.

In the configuration shown, the chassis 106 is secured to the first surface 116 of the first belt 102 and the first surface 120 of the second belt 104. In a configuration, the chassis may be secured to the second surface 118 of the first belt 102 and the second surface 122 of the second belt 104. Alternately, the chassis 106 may be secured to a first surface of one belt and a second surface of the other belt.

In each rescalable seam 112, a fastening component 114 is disposed between the first belt 102 and the second belt 104. The fastening component 114 may be composed of one or more mechanical fasteners (e.g., hook fasteners, hook and loop etc.) that releasably secure the first belt 102 to the second belt 104. Alternative fastening components 114 include contact adhesive, co-adhesive coatings, interlocking mechanical fasteners, magnetic closures, snaps, etc. Alternately, the fastening component 114 may be formed integral with the respective belt or printed onto the respective belt.

In the configuration shown, the second belt 104 overlaps the first belt 102 and the fastening component 114 thereby connects a second surface 118 of the first belt 102 to a first surface 120 of the second belt 104. It is also possible for the first belt 102 to overlap the second belt 104 and the fastening component 114 thereby connect the first surface 116 of the first belt 102 to the second surface 122 of the second belt 104. Alternately, the first belt 102 may overlap the second belt 104 on one side and the second belt 104 may overlap the first belt 102 on the other side. In the configuration shown, the first belt 102 is a front belt and the second belt 104 is a rear belt. However, the first belt 102 may be a rear belt and the second belt 104 may be a front belt.

In the configuration shown, the fastening component 114 is secured to the second surface 118 of the first belt 102 and mechanically secures to the second belt 104. Alternately, the fastening component 114 may be secured to the first surface 120 of the second belt 104 and mechanically secure to the first belt 102. In another configuration, the first rescalable side seam may be formed by a first element (not shown) of the fastening component 114 secured to one belt and a second element (not shown) of the fastening component 114 secured to the other belt. In such a configuration, the first element and the second element may be secured to each other to close the releasable side scam 112. In alternative configurations, the fastening component 114 is secured to the second surface 118 of the first belt 102, the second belt 104 is dispensed with, and the fastening component 114 is secured directly to the topsheet 106T of the chassis 106. Alternately, the fastening component 114 is secured to the first surface 120 of the second belt 104, the first belt 102 is dispensed with, and the fastening component 114 is secured directly to the backsheet 106B of the chassis 106.

Figure 2:
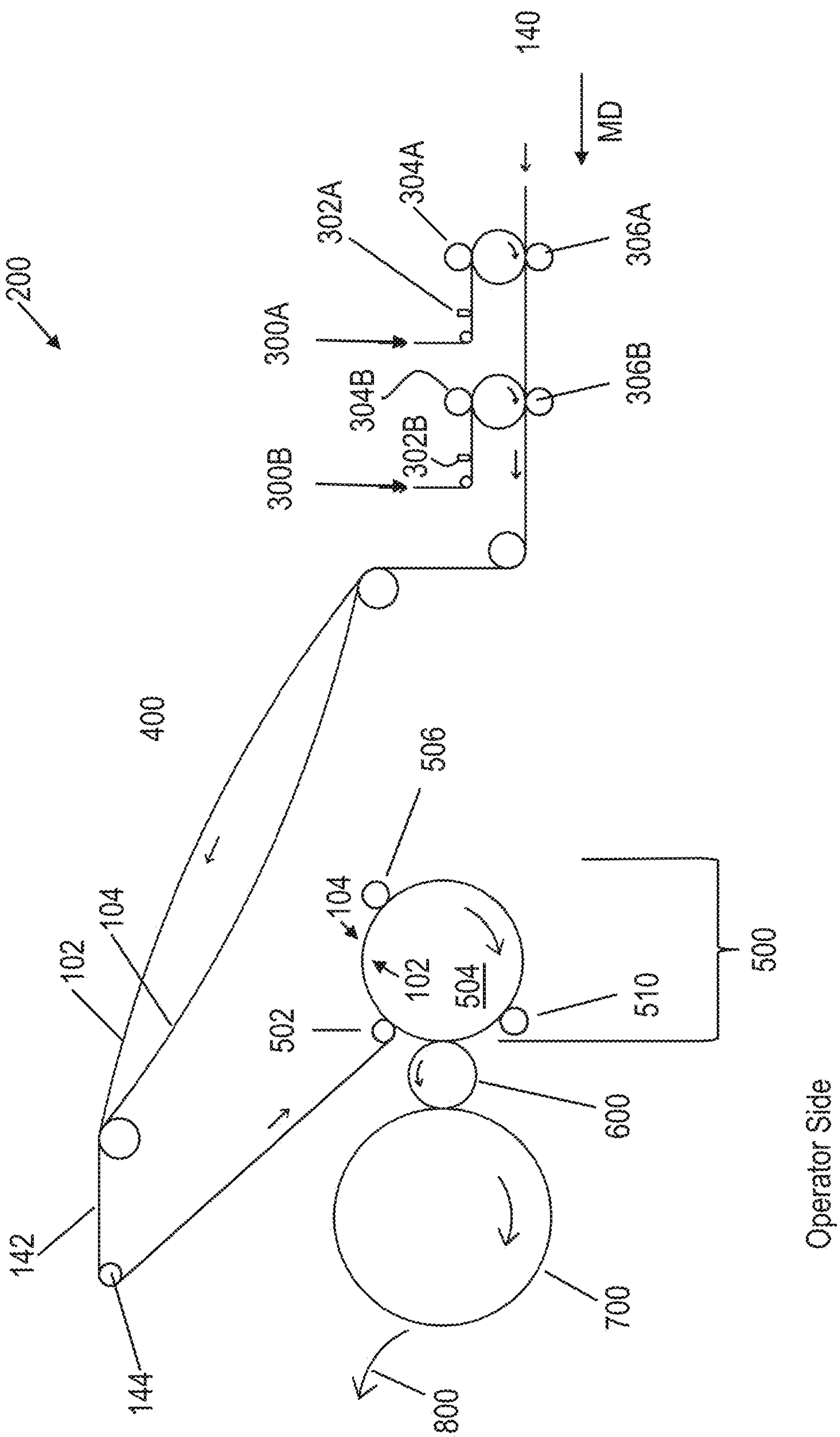
FIG. 2 is an example according to various configurations illustrating a schematic view of a production line used to manufacture the absorbent article from an operator side.

FIG. 2 is an example according to various configurations illustrating a schematic view of a production line 200 used to manufacture the absorbent article 100 from an operator side. A ladder web 140 (a.k.a., a substrate) is fed into the production line 200 in a machine direction MD and kept in tension within the production line 200. The ladder web 140 includes the first belt 102 (akin to a first side rail of a ladder), the second belt 104 (akin to a second side rung of a ladder), and the chassis 106 extending between the rungs. (See FIG. 3). Continuous fastener webs 300A, 300B are fed to respective adhesive applicators 302A, 302B and then to respective rotary knives 304A, 304B (knives 304A, 304B). The knives 304A, 304B cut the respective fastener webs 300A, 300B into fastening components 114 and the fastener cut and slips 306A, 306B apply the fastening component 114 to the first belt 102 only.

Each fastener cut and slip 306A, 306B applies its respective fastening component 114 to the first belt 102 a respective steady periodic rate of application. This results in uniform spacing between the fastening component 114 applied by cut and slip 306A, and uniform spacing between the fastening component 114 applied by cut and slip 306B. The fastening components 114 applied by cut and slip 306A are slightly offset from the fastening components 114 applied by cut and slip 306B. This results in an overall pattern of fastening components 114 applied by both fastener cut and slip 306A, 306B (as may be seen in FIG. 3), where upstream fasteners 114U are applied next to downstream fasteners 114D to form pairs of adjacent fasteners 114U, 114D separated by spaces.

As further seen in FIG. 2, the first belt 102 is farthest from the observer, the second belt 104 is nearest the observer, and the chassis 106 is between the first belt 102 and the second belt 104. The ladder web 140 with fastening components 114 continues to a bi-folder 400 that folds the (nearer) second belt 104 downward and then under the first belt 102 to form a folded ladder web 142 with the chassis 106 closest to the observer. A top view of the folded ladder web 142 may be seen at the top of FIG. 4. In an alternate configuration, the fastening component may be applied after the bi-folder 400.

The folded ladder web 142 is passed over an idler roller 144 and an infeed roller 502 of a belt overlapping hook seam apparatus 500 ("BOHS apparatus"). This inverts the folded ladder web 142 so that the first belt 102 rests on a folding drum 504 of the BOHS apparatus 500, the second belt 104 overlies the first belt 102, and the chassis 106 extends out of the page toward the observer. The inversion of the folded belt between the bi-folder 400 and the BOHS apparatus 500 is shown in FIG. 4.

The BOHS apparatus 500 separates the continuous folded ladder web 142 into discrete absorbent articles 100 and forms and seals the rescalable side seams 112. The BOHS apparatus 500 forms the rescalable side seams 112 by imparting a fold to each end of the first belt 102 that causes the respective fastening components 114 to face the second belt 104, and then seals the rescalable side seams 112 by abutting the fastening components 114 against the second belt 104. Seemed articles 800 are then fed to a transfer drum 600 and optionally to a pad turner 700.

Figure 3:
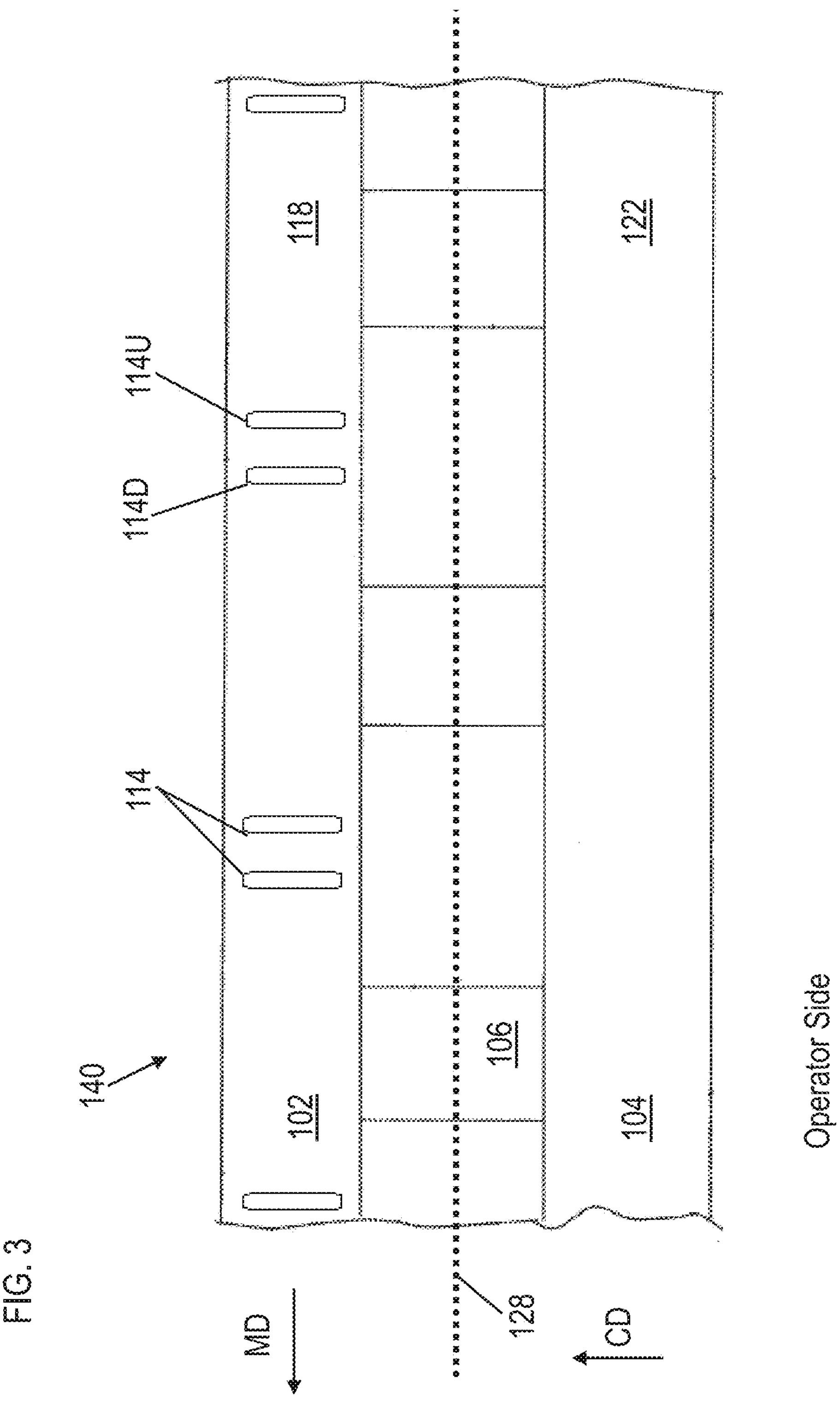
FIG. 3 is an example according to various configurations illustrating a schematic view of a ladder web that is fed into the production line of FIG. 2.

FIG. 3 is an example according to various configurations illustrating a schematic top view of the ladder web 140 that is fed into the production line 200 of FIG. 2. The ladder web 140 includes the first belt 102 with upstream fasteners 114U and downstream fasteners 114D secured to the second surface 118 thereof, the second belt 104 with the second surface 122 visible, and plural chassis 106. The plural chassis 106 are spaced periodically in the machine direction (MD) and each extends in a cross-machine direction (CD) and is secured to the first belt 102 and the second belt 104. The ladder web 140 is fed into the bi-folder 400.

Figure 4:
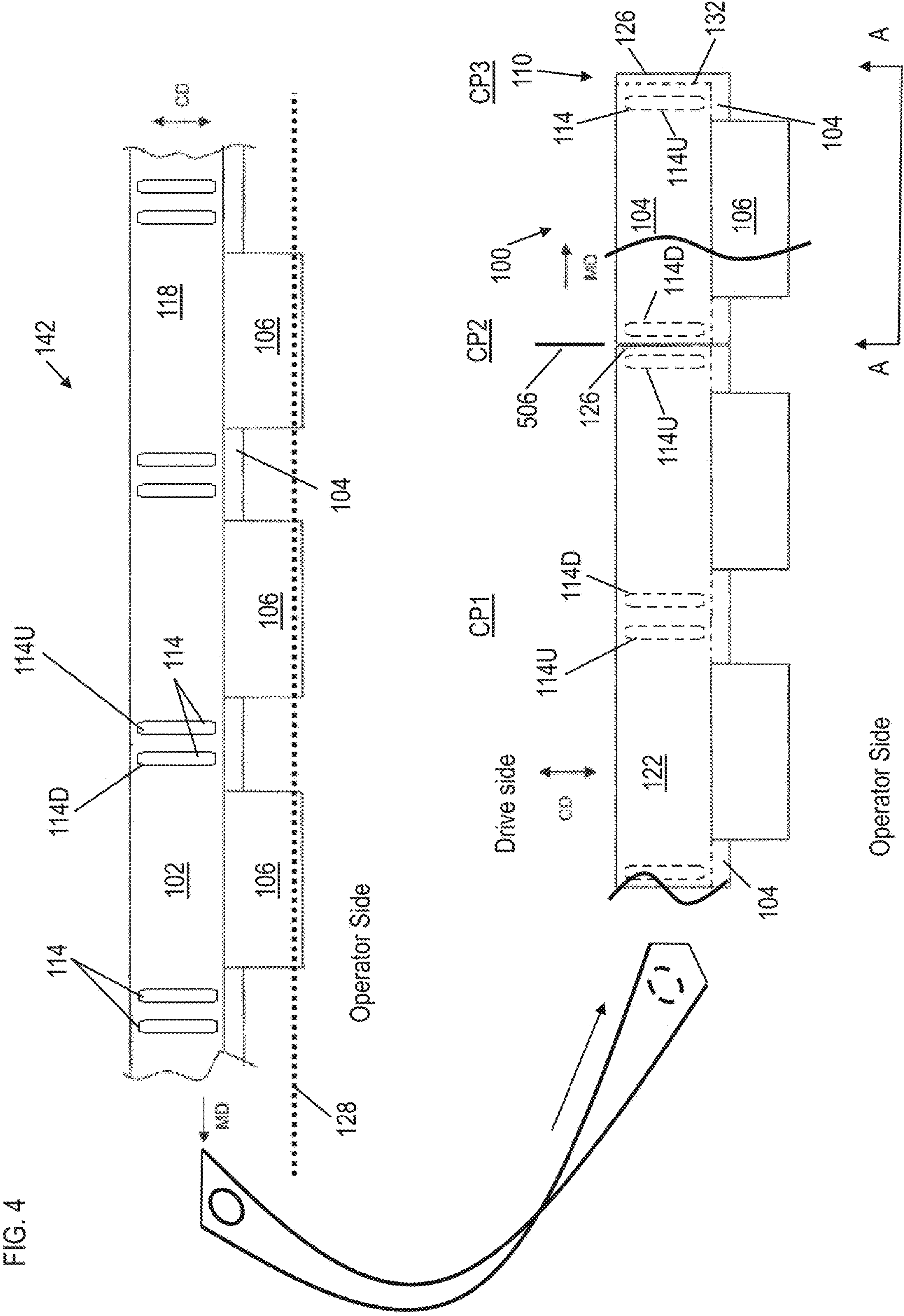
FIG. 4 is an example according to various configurations illustrating a schematic view of a progression of a folded ladder web during manufacture.

FIG. 4 is an example according to various configurations illustrating a schematic view of a progression of the ladder web 140 during manufacture. The (unfolded) ladder web 140 of FIG. 3 is fed into the bi-folder 400 where it is folded along the folding axis 128 to create the folded ladder web 142 seen at the top of FIG. 4. The folded ladder web 142 is inverted by the idler roller 144 and the infeed roller 502 of the BOHS apparatus 500 as is indicated by the arrow leading from the folded ladder web 142 at the top of FIG. 4 to the folded ladder web 142 at the bottom of FIG. 4. The bottom of FIG. 4 shows a linear top view of the folded ladder web 142 as the folded ladder web 142 wraps around the perimeter of the folding drum of the BOHS apparatus 500.

The folding drum 504 performs a variety of operations that occur as the folding drum 504 rotates. Each function may begin at one angular location and execute over a range of angular positions. Exemplary clocking positions CP1, CP2, CP3, CP4, CP5, CP0 have been designated herein (see FIG. 9) for illustrative purposes to capture snapshots of the operations of the folding drum 504 at respective fixed angular positions. Stated another way, the clocking positions are fixed angular positions and the progress of an operation at the respective angular position is shown. The clocking positions correspond to each other throughout the various figures, but the exact angle of a clocking position shown in one figure may be slightly different than the same clocking position in another figure.

As may be seen in FIG. 4, at clocking position CP1, the folded ladder web 142 is continuous. At clocking position CP2, a knife 506 cuts the first belt 102 and the second belt 104 and begins the folding process. At clocking position CP3, the folding process is nearly complete.

Figure 5:
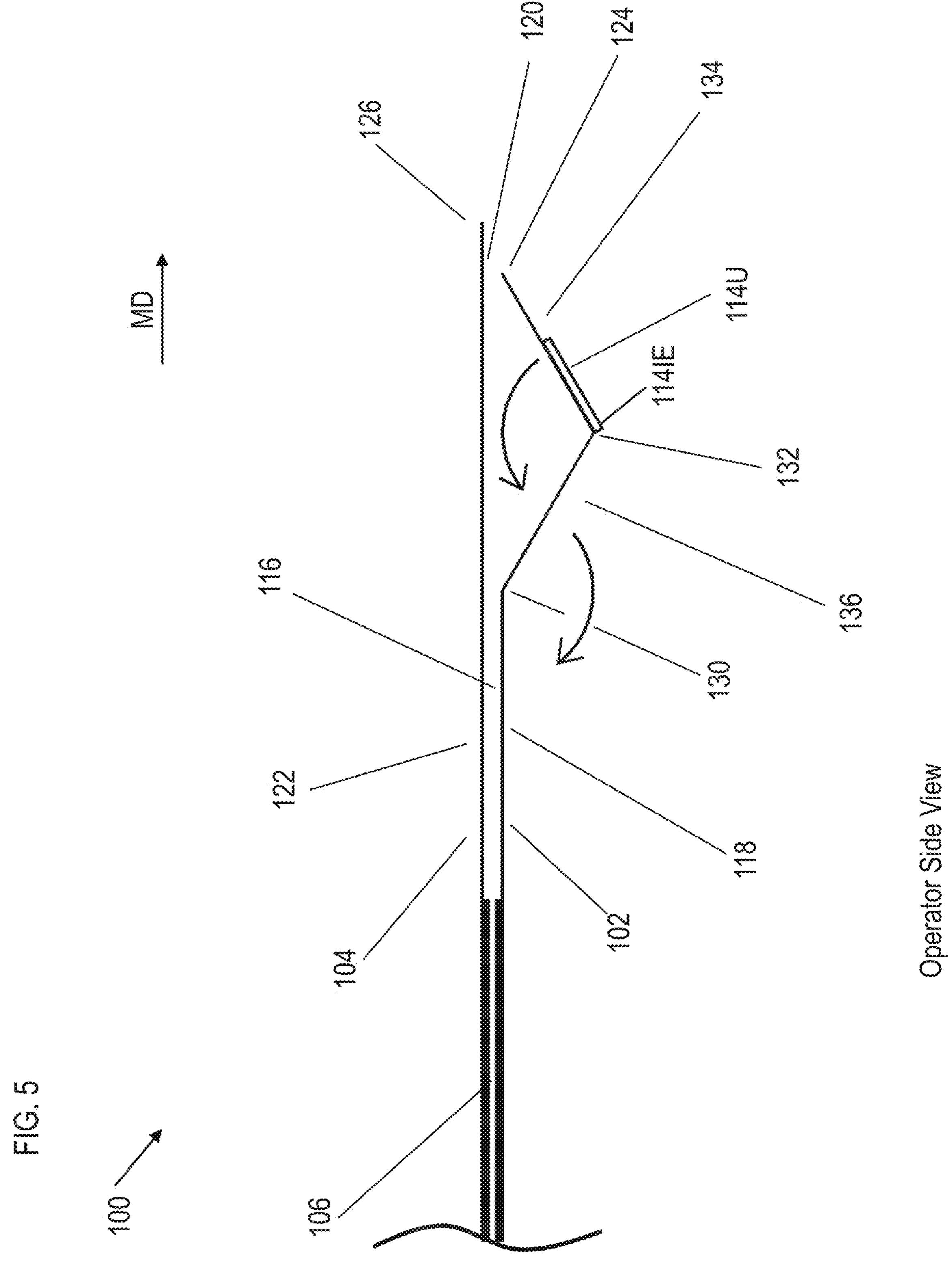
FIG. 5 is an example according to various configurations illustrating a view of the folded ladder web along line A-A of FIG. 4.

FIG. 5 is an example according to various configurations illustrating a view of the upstream cut end of a partially folded ladder web 142 along line A-A of FIG. 4 between clocking position CP2 and clocking position CP3. Visible are the first belt 102 (first outer region), the second belt 104 (second outer region), the chassis 106 (extending in the cross machine direction CD out of the page), the upstream (first) fastening component 114U, the first surface 116 and the second surface 118 of the first belt 102, the first surface 120 and the second surface 122 of the second belt 104, a first cut edge 124 of the first belt 102, a second cut edge 126 of the second belt 104, a first fold line 130, a second fold line 132, a first segment 134, and a second segment 136.

Figures 6A, 6B, 6C, 6D, 6E, 6F:
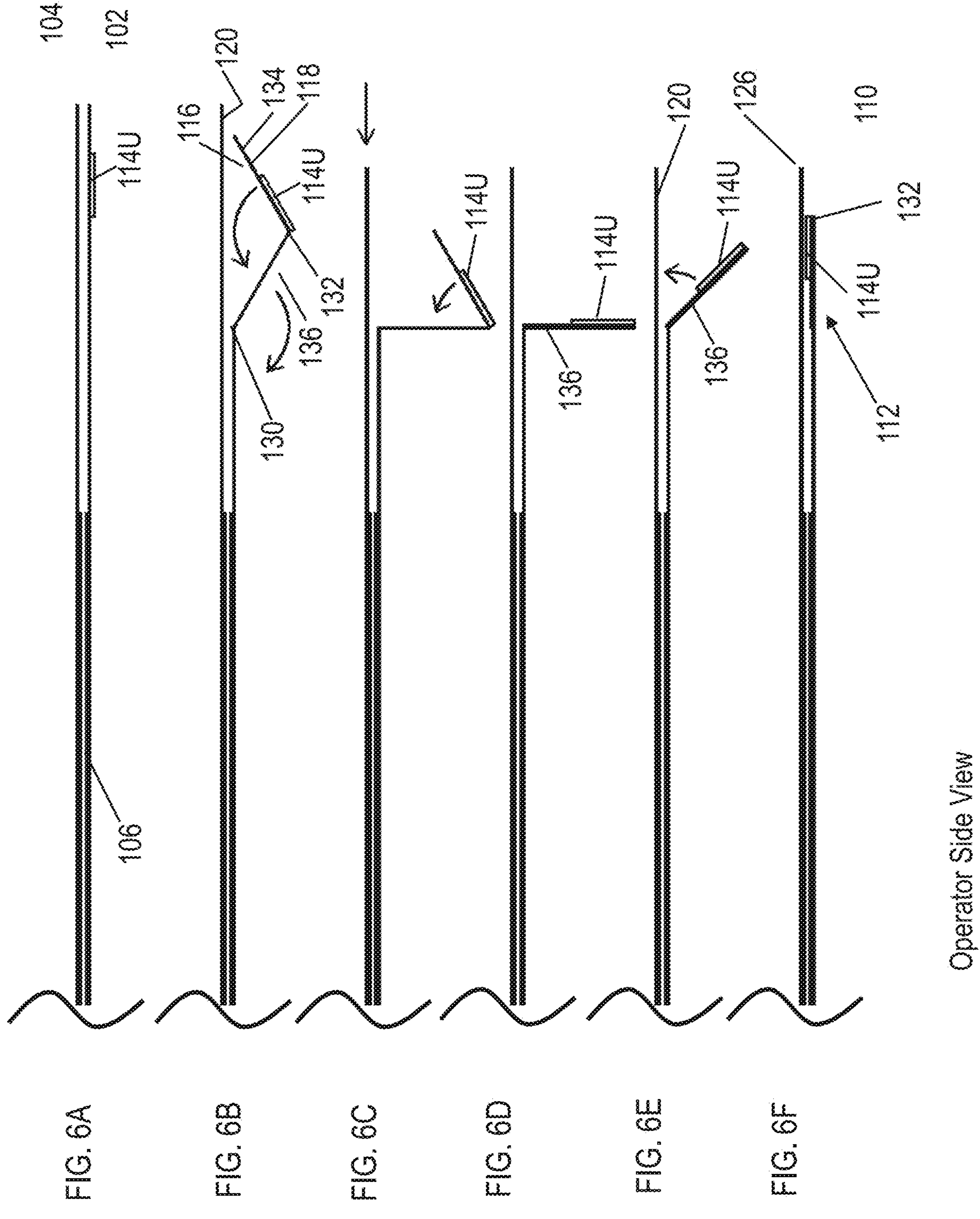
FIG. 6A to FIG. 6F are examples according to various configurations illustrating views along line A-A of a folding operation of the manufacturing process.

FIG. 6A to FIG. 6F are examples according to various configurations illustrating views along line A-A of a folding operation of the manufacturing process. FIG. 6A illustrates the first belt 102, second belt 104, the chassis 106, and the upstream (first) fastening component 114U at clocking position CP2 at the point of the cut by knife 506 and before folding is initiated. As seen in FIG. 6B and FIG. 6D, the first fold line 130 is achieved by folding the first segment 134 and the second segment 136 of the first belt 102 toward the second surface 118 of the first belt 102 at the first fold line 130. The second fold line 132 is achieved by folding the first segment 134 toward the first side 116 of the first belt 102. This collectively moves the first cut edge 124 of the first belt 102 away from the second belt 104, thereby causing an increased displacement therebetween. In this configuration, the first fold line 130 and a second fold line 132 are formed at least partly at the same time and the first fold line 130 and the second fold line 132 are formed with a minimal fold radius. The first fold line 130 is disposed between the upstream fastening component 114U and the chassis 106. In a configuration, a distance between the first fold line 130 and the first cut edge 124 of the first belt 102 may be at least twice a distance from the first cut edge 124 of the first belt 102 to an inboard edge 114IE of the upstream fastening component 114U. Alternately, the first fold line 130 may be achieved by manipulating the first belt to conform to a curved shape of constant or variable radius that gradually moves the first belt 102 away from the second belt.

The second fold line 132 is completed by folding the first segment 134 180 degrees around the second fold line 132 to abut the second segment 136 as seen in FIG. 6C and FIG. 6D. The second segment 136 must be folded around the first fold line 130 enough to prohibit contact between an end of the first segment 134 and the first surface 120 of the second belt 104. Alternately, the first belt 102 may be manipulated to conform to a curve to a curve with a constant or variable radius. In a configuration, the second fold line 132 will be disposed proximate the inboard edge 114IE of the upstream fastening component 114U.

As seen in FIG. 6E to FIG. 6F, the second segment 136 is unfolded (in a reverse direction) about the first fold line 130 until the upstream fastening component 114U comes into contact with the first surface 120 of the second belt 104. This contact causes temporary adhesion between the upstream fastening component 114U and the first surface 120 of the second belt 104, which seals the rescalable side seam 112. Pressure may be applied to the second surface 118 of the first belt 102 to squeeze the upstream fastening component 114U. This may better bed the upstream fastening component 114U to the first surface 120 of the second belt 104 to assure a strong temporary bond at the rescalable side seam 112.

As seen in FIG. 6C, the second belt 104 can be contracted from the original cut length in FIG. 6A. This results in the overlap 110, which provides a surface that may be grabbed to break the rescalable side seam 112. The overlap 110 can be minimized by allowing more contraction of the second belt 104. This will maximize the circumference of the belt and provide a looser fit. Alternatively, the overlap 110 can be maximized by preventing contraction of the second belt 104 which will result in a smaller belt circumference and a tighter fit.

This folding operation is disclosed in FIG. 6A to FIG. 6F as being applied proximate the leading edge of the first belt 102 and the second belt 104. However, the same or a similar process may be applied to the trailing edge as well, which will create both rescalable side seams 112 shown in FIG. 1.

Figures 7A, 7B, 7C, 7D, 7E, 7F, 7G:
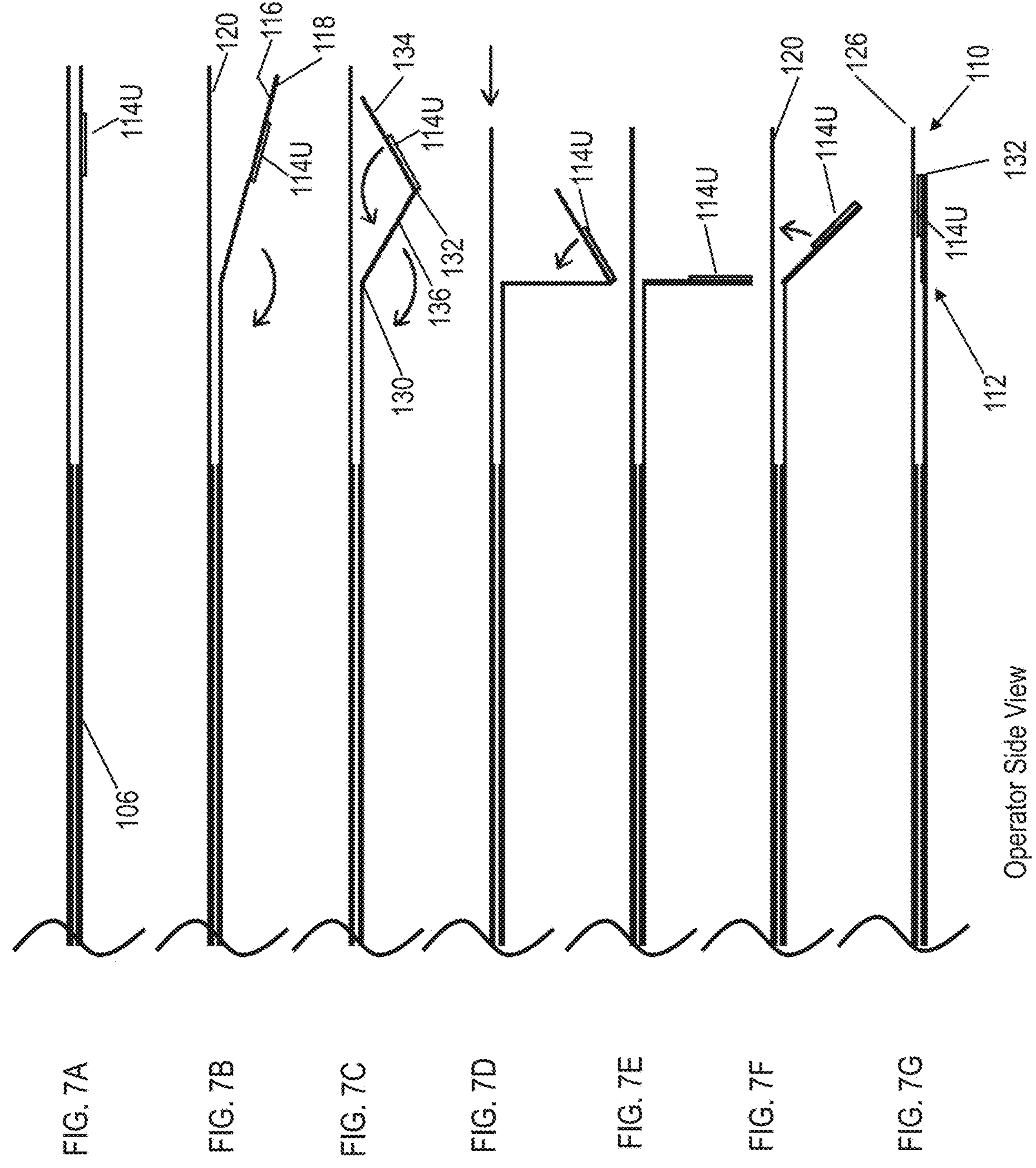
FIG. 7A to 7G are examples according to various configurations illustrating views along line A-A of an alternate folding operation of the manufacturing process from the operator side.
Figures 8A, 8B, 8C, 8D:
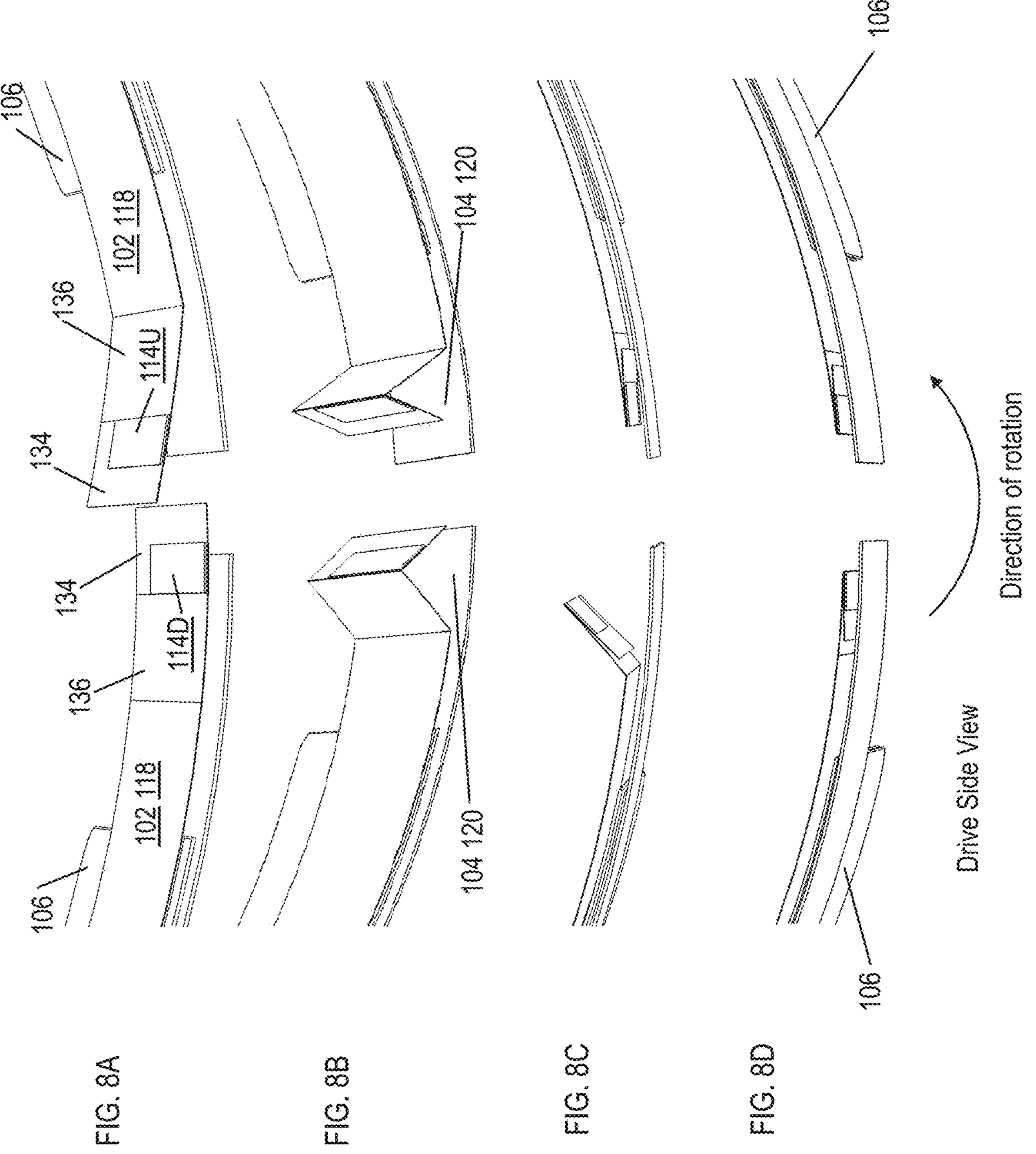
FIG. 8A to 8D are examples according to various configurations illustrating views of the second folding operation of FIG. 7A to 7G from a drive side from the operator side.

FIG. 7A to FIG. 7G are examples according to various configurations illustrating views along line A-A of an alternate folding operation of the manufacturing process. This folding process is similar to that of the folding process of FIG. 6A to FIG. 6F, except that FIG. 7B shows an intermediate step where the first segment 134 and the second segment 136 initially remain coplanar as the first segment 134 and the second segment 136 are pulled away from the second belt 104. This folding process can improve separation between the first belt 102 and second belt 104.

FIG. 8A to FIG. 8D are examples according to various configurations illustrating views of the second folding operation of FIG. 7A to FIG. 7G but from a rear/drive side. Like FIG. 6A to FIG. 7G, each of FIG. 8A to FIG. 8D shows a respective snapshot of the folding operation without regard for an associated clocking position at which the operation occurs. The first belt 102 and upstream fastening component 114U of FIG. 7A to FIG. 7G are now seen on the right in this drive (rear) side view. Also visible in this view is a first belt 102, a second belt 104, a chassis 106 (now facing into the page), and a downstream fastening component 114D of a downstream adjacent absorbent article 100 disposed downstream relative to the absorbent article 100 of FIG. 7A to FIG. 7G. FIG. 8A to FIG. 8D thereby illustrate the folding process occurring at both ends of each absorbent article 100.

Figure 9:
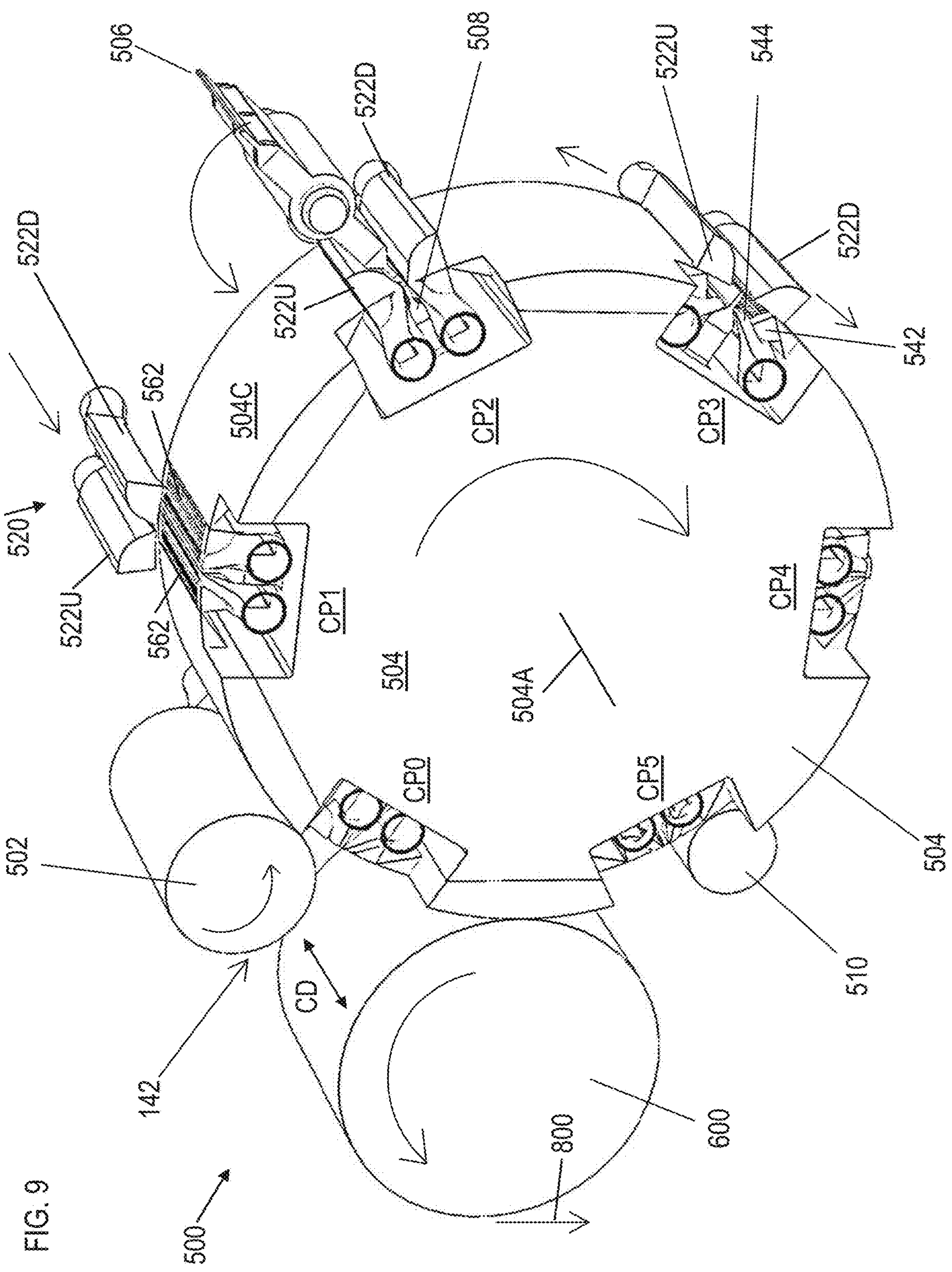
FIG. 9 is an example according to various configurations illustrating a belt overlapping hook seam apparatus that performs the folding operation from the operator side.
Figure 10:
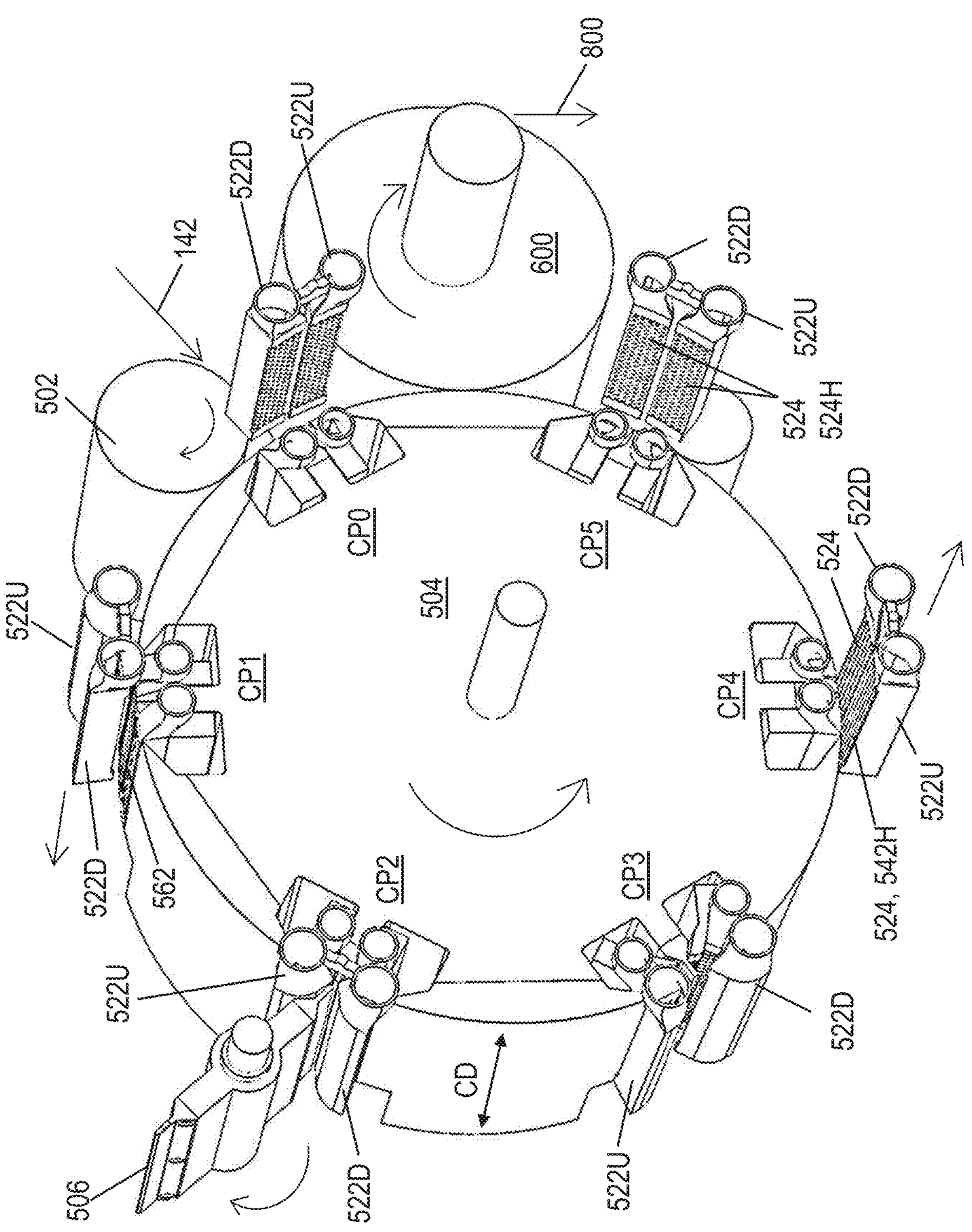
FIG. 10 is an example according to various configurations illustrating the belt overlapping hook seam apparatus of FIG. 9 from a drive side.

FIG. 9 is an example according to various configurations illustrating a belt overlapping hook seam apparatus 500 (BOHS apparatus 500) that performs the folding operation as seen from the operator side. FIG. 10 is an example according to various configurations illustrating the BOHS apparatus 500 from a drive (rear) side. The BOHS apparatus 500 includes a folding drum 504 that cuts the continuous folded ladder web 142 into discrete absorbent articles 100, separates the ends of the first belt 102 from the ends of the second belt 104, folds the ends of the first belt 102, and applies the fastening component 114 on each of the folded ends to the second belt 104, thereby forming and sealing the rescalable side scams 112.

The folded ladder web 142 is delivered to the rotating folding drum 504 under strain so that the clastic first belt 102 and the clastic second belt 104 are extended in the machine direction. The folded ladder web 142 is delivered such that the second surface 118 of the first belt 102 is in contact with the outer circumference 504C of the folding drum 504. Vacuum applied to holes in the outer circumferential surface 504C of the folding drum 504 holds the folded ladder web 142 against the outer circumferential surface 504C of the folding drum 504. The folded ladder web 142 remains continuous from the infeed roller 502 to a knife 506 disposed outside the folding drum 504 at clocking position CP2. The folding drum 504 includes integral anvils 508 at a periodic spacing having a period that corresponds to a cut length of the stretched first belt 102 and the stretched second belt 104. As the folding drum 504 rotates, the knife 506 counter rotates in synchronicity with the anvils 508. When the knife engages an anvil 508, the first belt 102 and the second belt 104 are cut. This cutting creates a discrete absorbent article 100 downstream of the cut. The knife 506 will cut between the upstream fastening component 114U and the downstream fastening component 114D that are attached to the second surface 118 (the bottom, abutting the outer circumferential surface 504C) of the first belt 102. Knife 506 is depicted as a rotary knife. Many alternate cutting techniques are possible, including rotary flex knife, rotary die cutter, axially translating slitter blade, laser cutting, water jet cutting, and ultrasonic cutting, etc. Alternatively, instead of a fully severing first belt 102 and second belt 104 with a cross-cut knife 506, the first belt 102 and the second belt 104 can be partially cross-cut with cross machine direction perforations. The partial crosscut can be completed upstream of the BOHS apparatus 500 or can be completed in stages prior to and integral to the BOHS apparatus 500. The incomplete cut or perforations can be severed in clocking position CP2.

In an alternate configuration, instead of a discrete upstream fastening component 114U and a discrete downstream fastening component 114D being applied by the fastener cut and slips 306A, 306B, an appropriately sized and positioned single fastening component (not shown) may be applied and cut into the upstream fastening component 114U and the downstream fastening component 114D by the knife 506 during the cutting operation.

Vacuum supplied through vacuum holes 562 near the anvil 508 generates frictional force between the folding drum 504 and the second surface 118 of the first belt 102. The frictional force resulting from the vacuum applied by the folding drum 504 prevents the elastics in the first belt 102 from contracting and keeps the first belt 102 stretched. Vacuum is supplied to the holes in the outer circumferential surface 504C of the folding drum 504 and to the vacuum holes 562 by vacuum supply passages (not shown) internal to folding drum 504. The vacuum can be supplied to the folding drum 504 by a pipe or hose to an external vacuum source such as a fan, blower, or pump. The vacuum can alternatively be generated internal to the folding drum 504 by an internal fan, blower, or pump. The flow rate and pressure of the vacuum supplied to the vacuum holes in the outer circumferential surface 504C of the folding drum 504 and the vacuum holes 562 can be varied with rotational position of the folding drum 504. Rotational control of the vacuum supply and shut off timing can be accomplished with a rotary vacuum manifold or valves that are mechanically, pneumatically, or electrically actuated based on folding drum 504 rotation.

In a configuration, the second belt 104 can also be held by the vacuum that causes air to flow through porosities in the first belt 102 and generates a frictional force between the first surface 116 of the first belt 102 and the first surface 120 of the second belt 104. This frictional force may be used to prevent or control contraction of the second belt 104 due to clastic forces after the second belt 104 has been cut. The amount of contraction is dependent at least on the coefficient of friction between the first surface 116 of the first belt 102 and the first surface 120 of the second belt 104 as well as a porosity of the first belt 102 and a porosity of the second belt 104. This contraction step may be before, during, or after folding of the first belt 102. The second belt 104 can alternatively be held externally by friction, vacuum, or grippers from an externally controlled finger or belt.

In the configuration shown, more positive control of the second belt 104 may be achieved using a BOHS apparatus 500 that includes a second belt control finger assembly 520 having an upstream finger 522U and a downstream finger 522D. The upstream finger 5222U and the downstream finger 522D (fingers 522U, 522D) orbit with rotation of the folding drum 504. The upstream finger 522U is oriented to coincide with an upstream side of the anvil 508 and the downstream finger 522D is oriented to coincide with a downstream side of the anvil 508. As disclosed herein, "retract" means moving in the cross-machine direction CD toward the drive side and toward a "retracted position" in which a finger is disposed laterally outside cross-machine direction planes bounding the bi-folded continuous ladder web. Similarly, "extend" means moving in the cross-machine direction CD toward the operator side and toward an extended position in which a finger is disposed above and axially aligned with the folding drum 504. Alternatively, the retract direction could be in the cross-machine direction CD toward the operation side and the extend direction could be in the cross-machine direction CD toward the drive side.

At clocking position CP5, the fingers 522U, 522D are configured to retract to avoid the transfer drum 600, the infeeding folded ladder web 142, and the infeed roller 502 as the fingers 522U, 522D orbit around a folding drum axis 504A. Between clocking position CP1 and clocking position CP2, the fingers 522U, 522D are configured to extend to the extended position over the folding drum 504. The fingers 522U, 522D engage the second surface 122 of the second belt 104 while the second belt 104 is uncut and stretched. The engagement of the fingers 522U, 522D can be created by reducing the radius of orbit for both fingers 522U, 522D so that they travel radially inward towards the folding drum 504. The fingers 522U, 522D can move into contact with the second surface 122 of the second belt 104 or the fingers 522U, 522D may be in proximity of the second surface 122 of the second belt 104 for engagement. Control finger vacuum zones 524 on the fingers 522U, 522D include control finger vacuum zones holes 524H supplied with vacuum and generate a frictional force between the second surface 122 of the second belt 104 and the fingers 522U, 522D. The geometry of the second belt 104 is configured to allow the rotating knife 506 to pass between the fingers 522U, 522D and contact the anvil 508 in the folding drum 504, which cuts the first belt 102 and the second belt 104. The friction against the fingers 522U, 522D maintains control of the cut ends of the second belt 104 and prevents the second belt 104 from contracting due to elastic forces after the second belt 104 has been cut.

Axial displacement to extend and retract the fingers 522U, 522D may be achieved by a retraction mechanism (not shown) integrated with the rotating folding drum 504. In a configuration, a stationary mechanical barrel cam is coaxial with the folding drum 504. As the folding drum 504 rotates, a cam follower attached to the second belt control finger assembly 520 is axially displaced by the groove cut in the barrel cam. A geometry of the barrel cam groove is configured to move the fingers 522U, 522D into the retracted position between clocking position CP5 and clocking position CP1 and dwell there until around clocking position CP1 to avoid the transfer drum 600, the infeeding folded ladder web 142, and the infeed roller 502. The barrel cam groove is further configured to then extend the fingers 522U, 522D into the extended position prior to the cut at clocking position CP2 and dwell there until and after the fastening components 114 contact the first surface 120 of the second belt 104 to close the rescalable side seam 112, which occurs between clocking position CP3 and clocking position CP4. In a configuration, the motion between the retracted position and the extended position is controlled by an engineered cam motion such as a 3-4-5 polynomial. The diameter and number of article positions on the folding drum 504 may be adjusted to provide enough time for modest peak acceleration during the cam motion. Radial displacement of the fingers 522U, 522D to drive proximity with the second surface 122 of the second belt 104 can be accomplished with a radial cam that controls the radial displacement of the fingers 522U, 522D with rotation of the folding drum 504. Alternatively, the axial motions of the barrel cam to extend the fingers 522U, 522D can also create inward radial displacement of the fingers 522U, 522D through a linkage mechanism.

In the configuration shown, each end of the second belt 104 is contracted in length slightly to adjust the end amount of material that will form the overlap 110. More contraction will result in a smaller overlap 110, so some contraction is desirable to avoid a large overlap 110 and corresponding lower belt circumference of the assembled seemed absorbent article 100. When the fingers 522U, 522D are in control of the cut ends of the second belt 104, the precise amount of contraction of the second belt 104 may be achieved by adjusting the orbital position of the fingers 522U, 522D relative to the folding drum 504 and the anvil 508. As used herein, "orbiting motion" of the fingers 522U, 522D around the folding drum axis 504A equates to circumferential motion of the fingers 522U, 522D relative to the folding drum 504 and the anvil 508. In other words, an adjustment of a phase angle of each finger 522U, 522D around the folding drum 504 axis of rotation.

The orbiting motion of the fingers 522U, 522D may be achieved and precisely controlled by a control finger orbit adjusting mechanism (not shown). In a configuration, the control finger orbit adjusting mechanism includes a mechanical linkage and a mechanical radial cam. Each finger 522U, 522D is attached to a rotational bearing that allows the control finger orbit adjusting mechanism to orbit with and adjustable the phase angle around the folding drum 504 axis of rotation. The mechanical radial cam is stationary. A cam follower attached to the control finger orbit adjusting linkage engages with the mechanical radial cam. The cam follower and control finger orbit adjusting linkage rotate with the folding drum 504. The rotation of the folding drum 504 will radially displace the cam follower based on an engineered cam profile of the mechanical radial cam. The cam follower is connected by pins to two links that are pinned to each finger 522U, 522D. As the cam follower is displaced radially outward, this motion pushes the shared pin joint of the two links which increases an included angle between the links and forces the fingers 522U, 522D to orbit further apart (i.e., to each move farther from the anvil 508). This results in an increase in an arc distance between the anvil 508 and the fingers 522U, 522D. This allows controlled contraction of the ends of the second belt 104. This contraction step should be after separation of the first belt 102 from the second belt 104 and may be during or after folding of the first belt 102.

Figure 11:
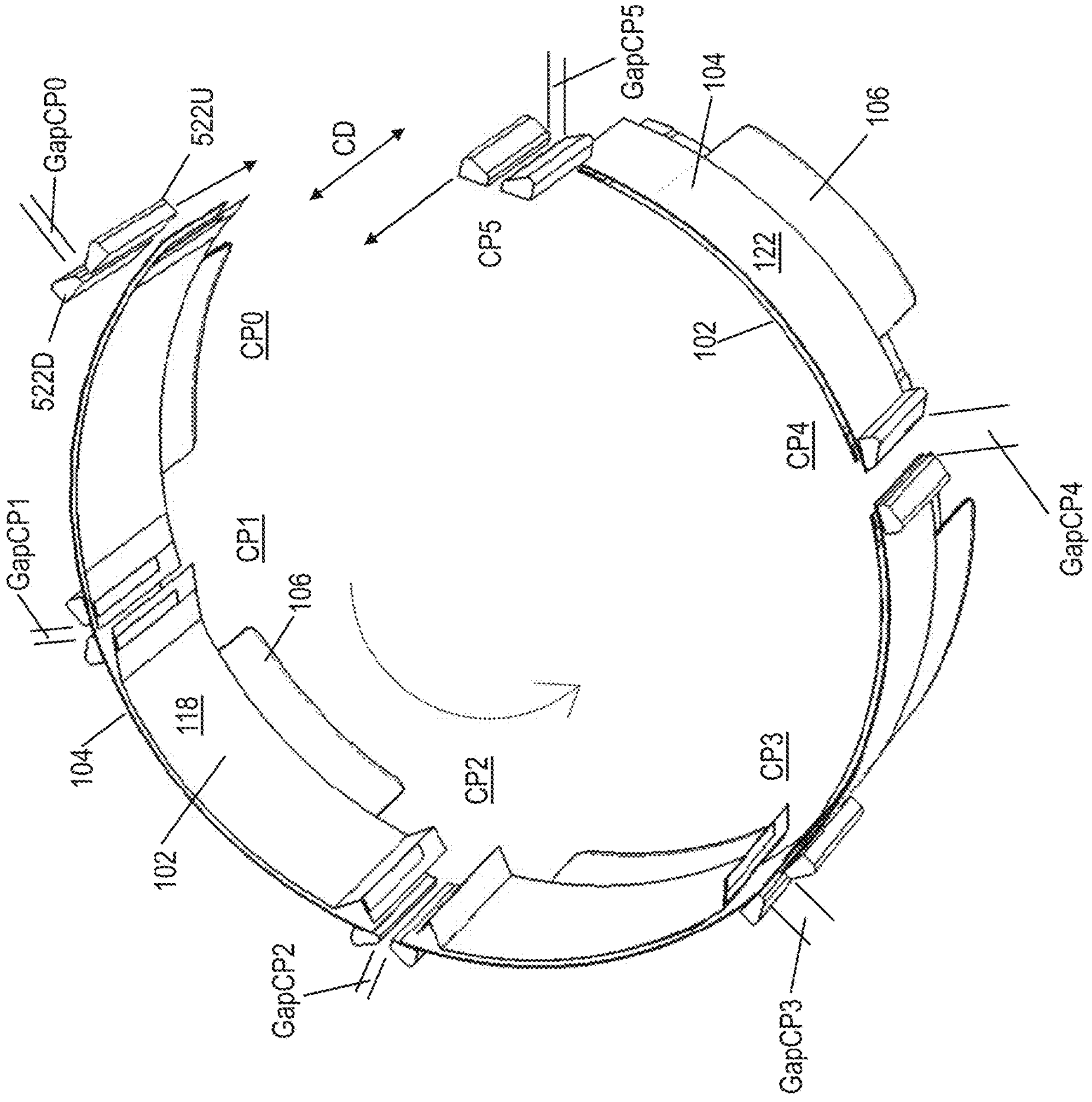
FIG. 11 is an example according to various configurations schematically illustrating operations of the belt overlapping hook seam apparatus of FIG. 9 from the drive side during the folding operation.

This relative orbiting (relative circumferential movement, phase angle adjustment) may be seen in FIG. 11, which is an example according to various configurations schematically illustrating operations of the belt overlapping hook seam apparatus 500 from the drive side. FIG. 11 shows gaps GapCP0 to GAPCP5 between the fingers 522U, 522D at various clocking positions CP0 to CP5. At clocking position CP2, the gap GAPCP2 during and after the cutting operation is controlled to be relatively small. At clocking positions CP3 and CP4, the gaps GapCP3, GapCP4 are made relatively large via the control finger orbit adjusting mechanism. The relatively large gaps GapCP3, GapCP4 cause the controlled contraction of the second belt 104 and associated controlled overlap 110 present in the assembled and seamed absorbent article 100.

Figure 12:
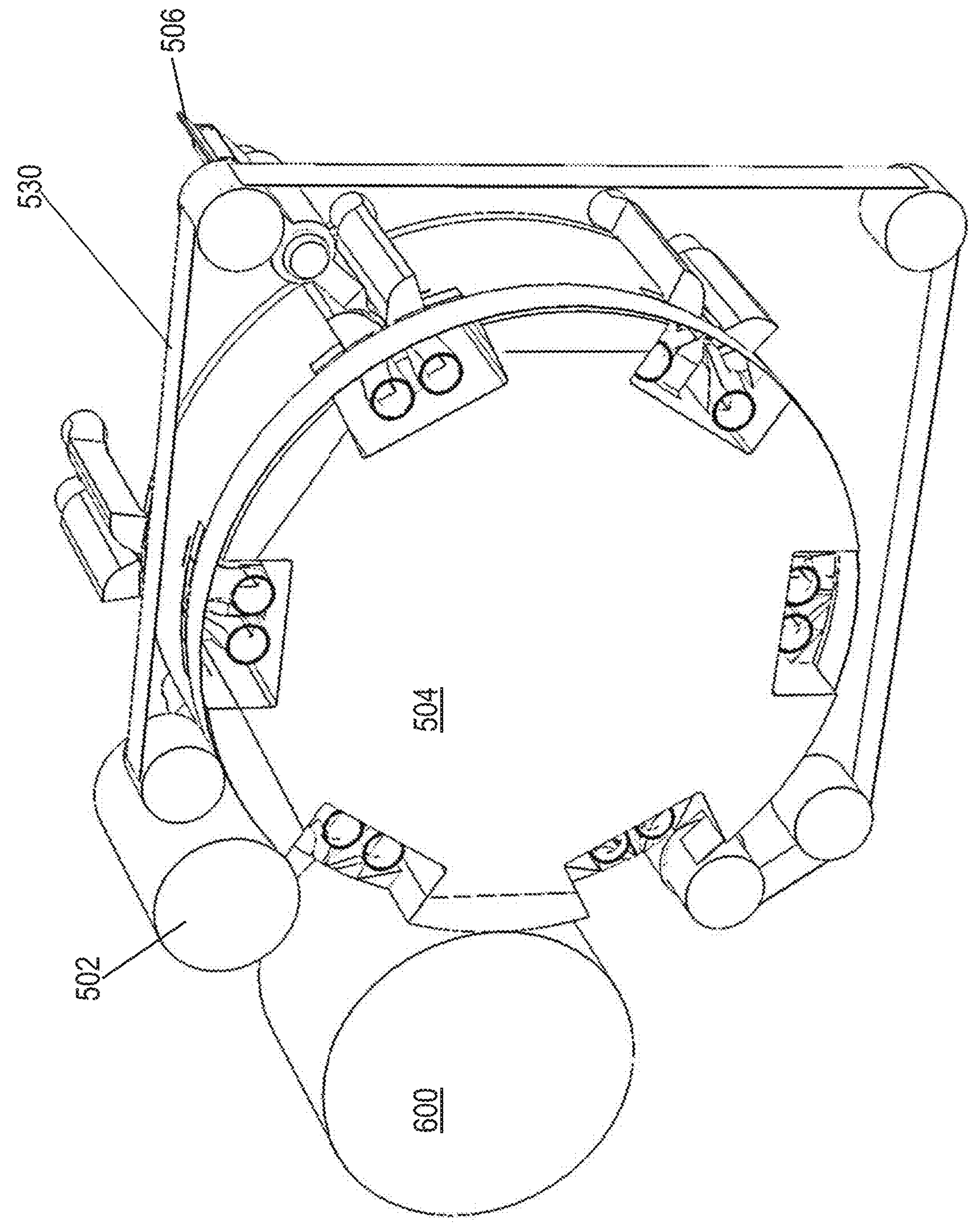
FIG. 12 is an example according to various configurations schematically illustrating an article control belt of the belt overlapping hook seam apparatus from the operator side.

FIG. 12 is an example according to various configurations schematically illustrating an article control belt 530 of the belt overlapping hook seam apparatus 500 from the operator side. The article control belt 530 may be used alone or in conjunction with the second belt control finger assembly 520. The article control belt 530 is wrapped partially around the outer circumferential surface 504C of the folding drum 504 and holds the chassis 106 of the absorbent article 100 against the outer circumferential surface 504C of the folding drum 504. The article control belt 530 is axially displaced in the cross-machine direction CD toward the operator side from the first belt 102 and the second belt 104 and does not interfere with the knife 506 or the second belt control finger assembly 520. The article control belt 530 can engage the absorbent article 100 between the infeed roller 502 and the knife 506 and can disengage from the absorbent article 100 before the absorbent article 100 reaches the transfer drum 600.

Figure 13:
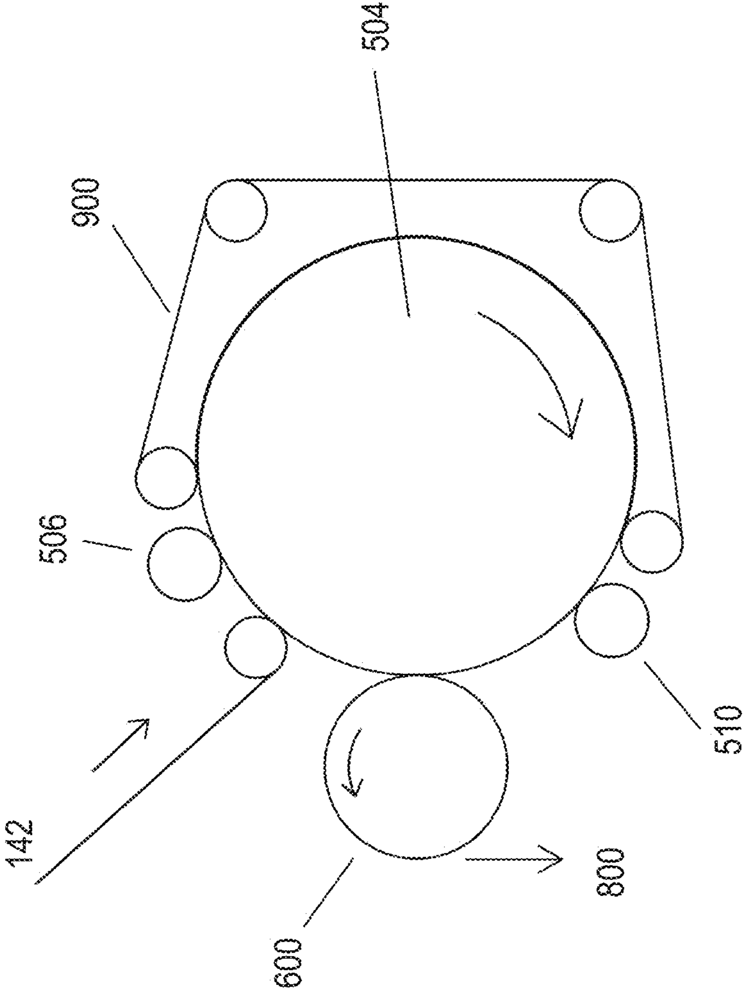
FIG. 13 is an example according to various configurations schematically illustrating a separation belt of the belt overlapping hook seam apparatus from the operator side.

FIG. 13 is an example according to various configurations schematically illustrating a separation belt 900 of the BOHS apparatus 500 from the operator side. The separation belt 900 is an alternative to the second belt control finger assembly 520 for controlling contraction. The separation belt 900 wraps around the folding drum 504 from after the knife 506 to before the transfer drum 600 and is perforated with vacuum holes (not shown). The separation belt 900 is driven at matched surface speed with the outer circumferential surface 504C of the folding drum 504. A vacuum is supplied from a concave external vacuum manifold (not shown) to supply the vacuum to a surface of the separation belt 900 facing the folding drum 504. After the second belt

104 is cut, the second belt 104 is held by the vacuum against the separation belt 900. The separation belt 900 controls the ends of the second belt 104 by controlling the amount of friction and an associated frictional force between the separation belt 900 and the second surface 122 of the second belt 104. Reducing the vacuum and associated frictional force causes the second belt 104 to contract under elastic forces. This, in turn, allows the separation belt 900 to control the amount of clastic contraction and associated overlap 110 in the seamed absorbent article 100.

Figure 14:
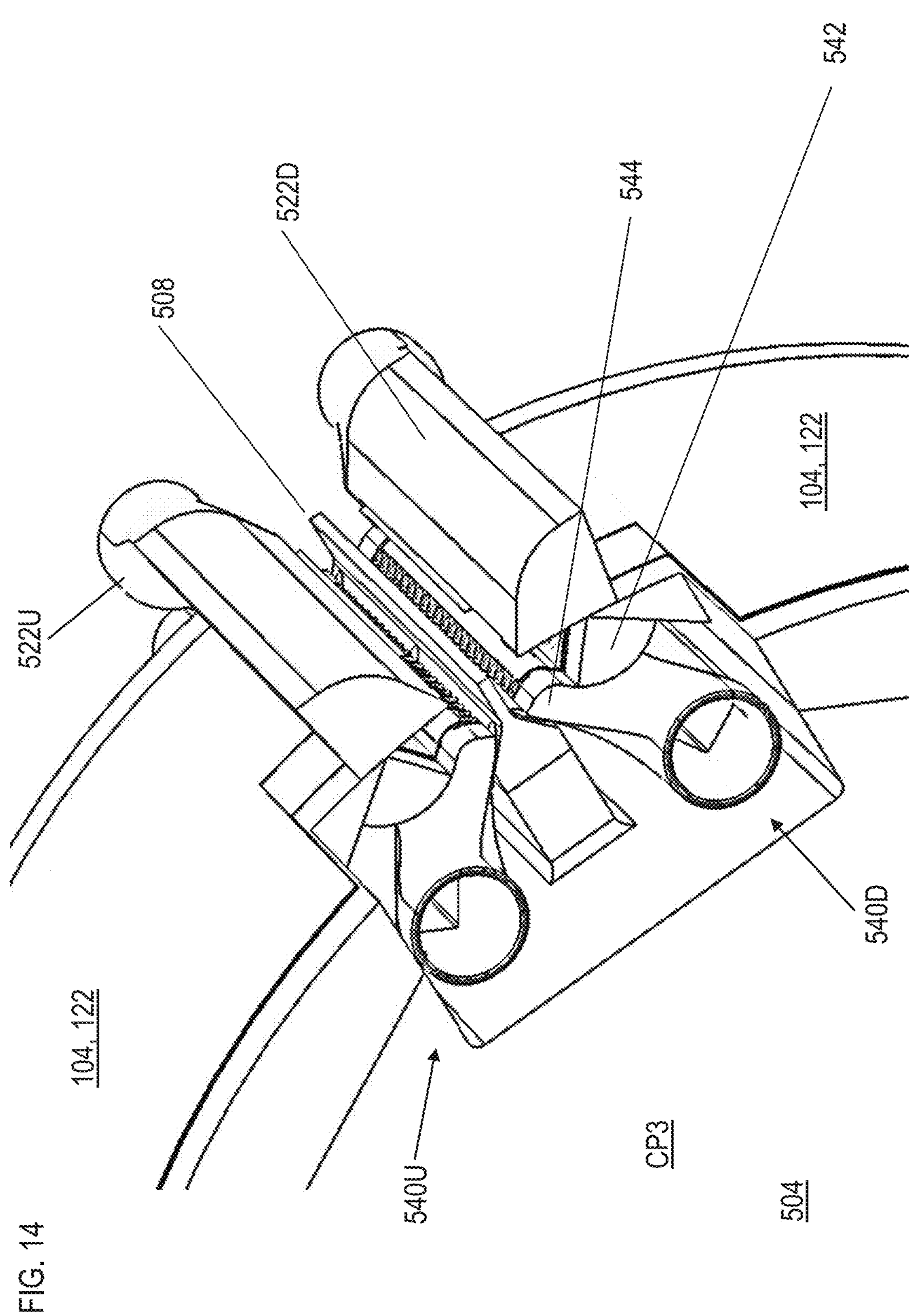
FIG. 14 is an example according to various configurations schematically illustrating aspects of a folding drum of the belt overlapping hook seam apparatus at a point during the folding operation from the operator side.
Figure 15:
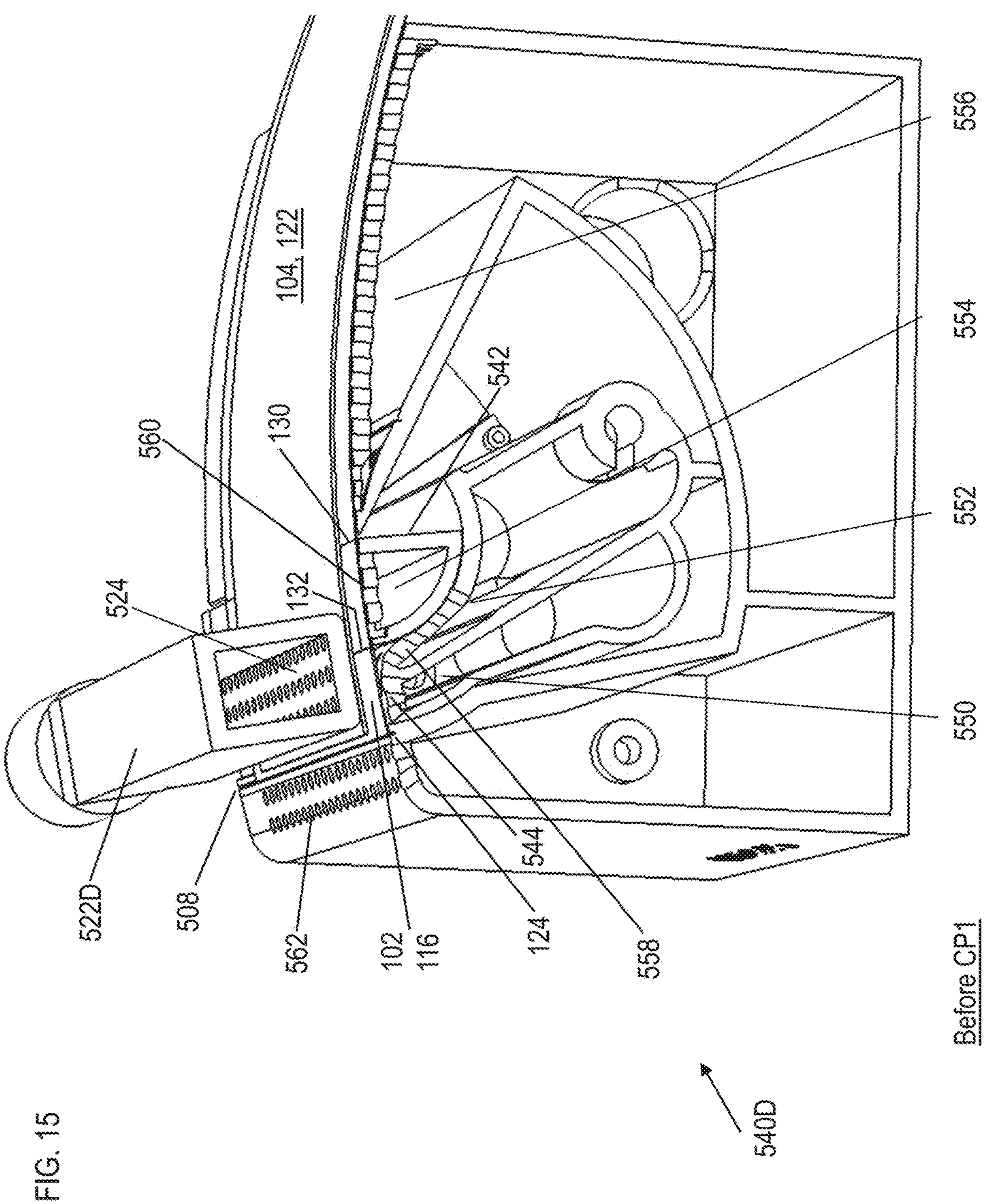
FIG. 15 to FIG. 18 are examples according to various configurations schematically illustrating views of a downstream folding mechanism of the folding drum of FIG. 14 in various stages of the folding process from the operator side.

FIG. 14 is an example according to various configurations schematically illustrating aspects of a folding drum 504 of the belt overlapping hook scam apparatus 500 at clocking position CP3. A folding mechanism 540 includes an upstream folding mechanism 540U disposed under the upstream finger 522U and a downstream folding mechanism 540D disposed under the downstream finger 522D. The upstream folding mechanism 540U is responsible for folding a respective end of the first belt 102 disposed between the upstream folding mechanism 540U and the upstream finger 522U as the folding drum 504 rotates through the various clocking positions. The downstream folding mechanism 540D is responsible for folding a respective end of the first belt 102 disposed between the downstream folding mechanism 540D and the downstream finger 522D as the folding drum 504 rotates through the various clocking positions. As may be seen in FIG. 11, the folding operations begin slightly before clocking position CP1 and finish after clocking position CP3.

FIG. 15 to FIG. 18 are examples according to various configurations schematically illustrating views of the downstream folding mechanism 540D of the folding drum 504 of FIG. 14 in various stages of the folding process from the operator side. In FIG. 15 to FIG. 18, both the first belt 102 and the second belt 104 are visible. In the configuration shown, the downstream folding mechanism 540D works in conjunction with the downstream finger 522D. Vacuum applied to the second surface 122 of the second belt 104 by the downstream finger 522D allows the downstream finger 522D to maintain positive control of the second belt 104 and hold the end of the second belt 104 during separation from the first belt 102. Vacuum applied to the second surface 122 of the second belt 104 by the downstream finger 522D allows the downstream finger 522D to control an amount of contraction as disclosed above while the downstream folding mechanism 540D executes the folding operation thereunder. However, alternate techniques for controlling the second belt 104 such as those described above may be used in conjunction with the downstream folding mechanism 540D. In this configuration, the structure and function for the upstream folding mechanism 540U and the upstream finger 522U are a partial or complete mirror image of that shown for the downstream folding mechanism 540D and downstream finger 522D shown.

The downstream folding mechanism 540D includes a folding finger 542 and a separation finger 544. The actuation of the separation finger 544 and the folding finger 542 may be achieved by an internal cam actuated mechanism (not shown) inside of the folding drum 504. Alternatively, an independent actuation of the separation finger 544 and the folding finger 542 may be driven by rotary motors, pneumatic actuation, linear motors, hydraulic actuation, etc.

Vacuum applied to the separation finger 544 and a separate flow of vacuum supplied to the folding finger 542 retain positive control on the second surface 118 of the first belt 102. Timing of vacuum and positive air to various control surfaces on the folding drum 504 may be controlled relative to the rotation of the folding drum 504 by a stationary vacuum manifold (not shown) that varies vacuum supplied as a function of a folding drum rotation angle. Vacuum and positive air pressure can also be supplied and timed by electrically controlled valves, valves controlled by a rotational cam mechanism, or pneumatically actuated control valves (not shown).

Figure 16:
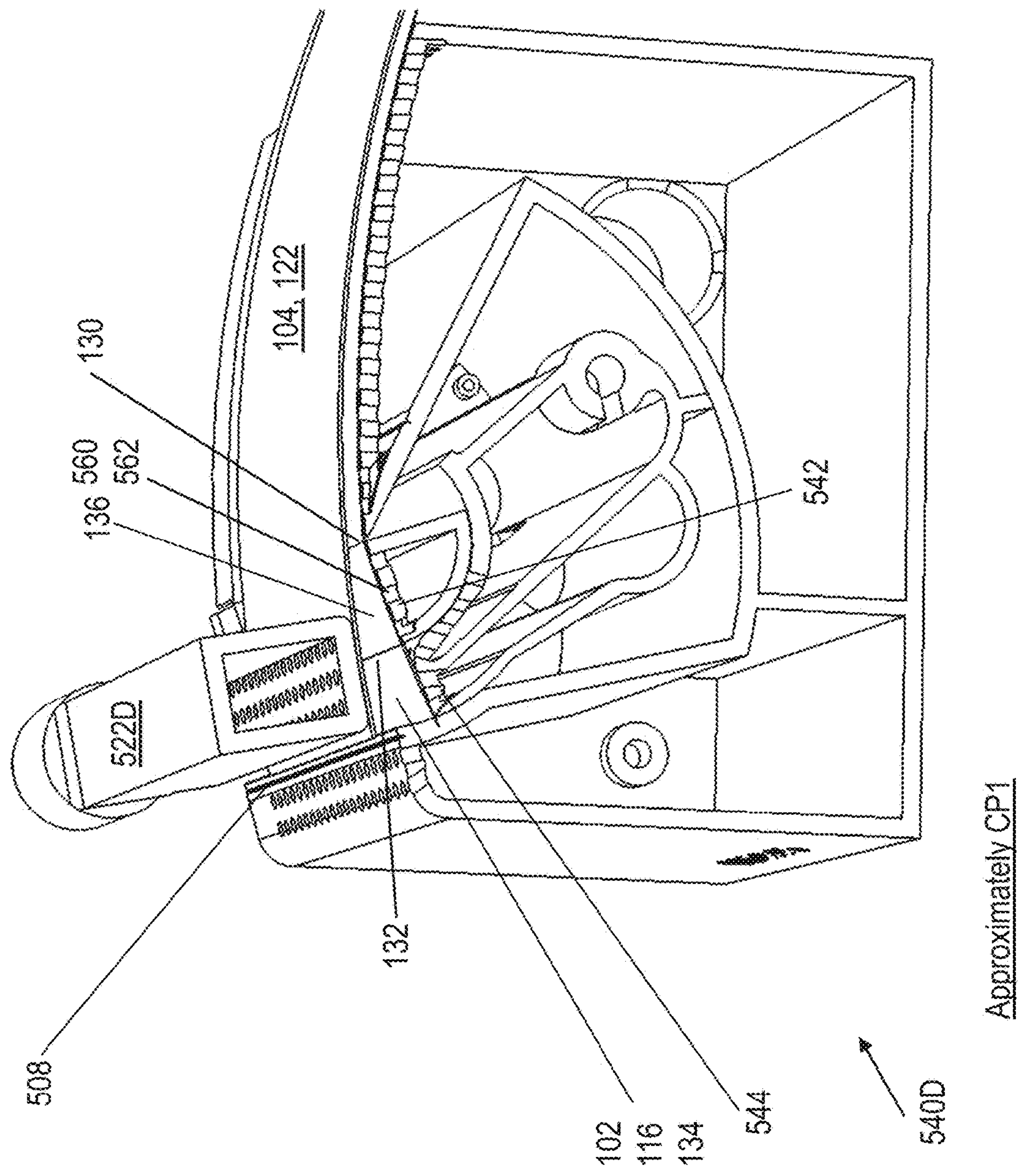

Vacuum applied to the separation finger 544 controls the first segment 134 of the first belt 102 and vacuum supplied to the folding finger 542 controls the second segment 136 of the first belt 102. To separate the ends of the first belt 102 and the second belt 104, the separation finger 544 and the folding finger 542 are both actuated by a mechanism (not shown) integral to the folding drum 504 that cause both the separation finger 544 and the folding finger 542 to rotate around the first fold line 130. The separation finger 544 and the folding finger 542 can rotate with the same rotational displacement such that the separation finger 544 and the folding finger 542 and the first segment 134 and the second segment 136 remain co-planar as is detailed in FIG. 7A to FIG. 7B. This results in the first fold around the first fold line 130 as shown in FIG. 16. Once rotation of ends of the separation finger 544 and the folding finger 542 has achieved substantial separation between the first belt 102 and the second belt 104, a second fold begins by actuating the folding finger 542 to rotate the first segment 134 around the second fold line 132. Alternately, the initial rotational displacement of the separation finger 544 may be slowed relative to the folding finger 542 to initiate the second fold line 132 around the first fold line 132 as is detailed in FIG. 6A to FIG. 6B.

Figure 17:
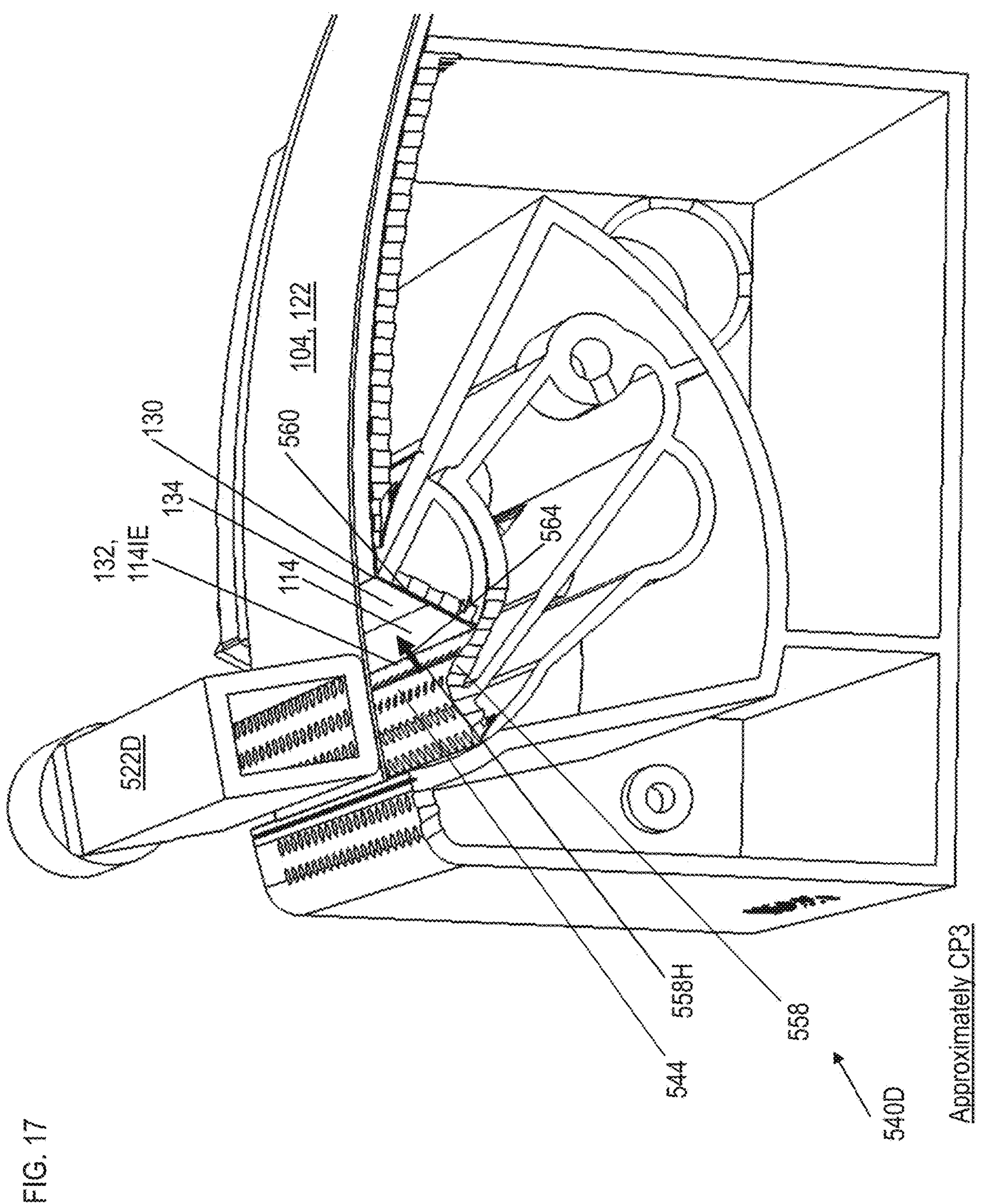
Figure 18:
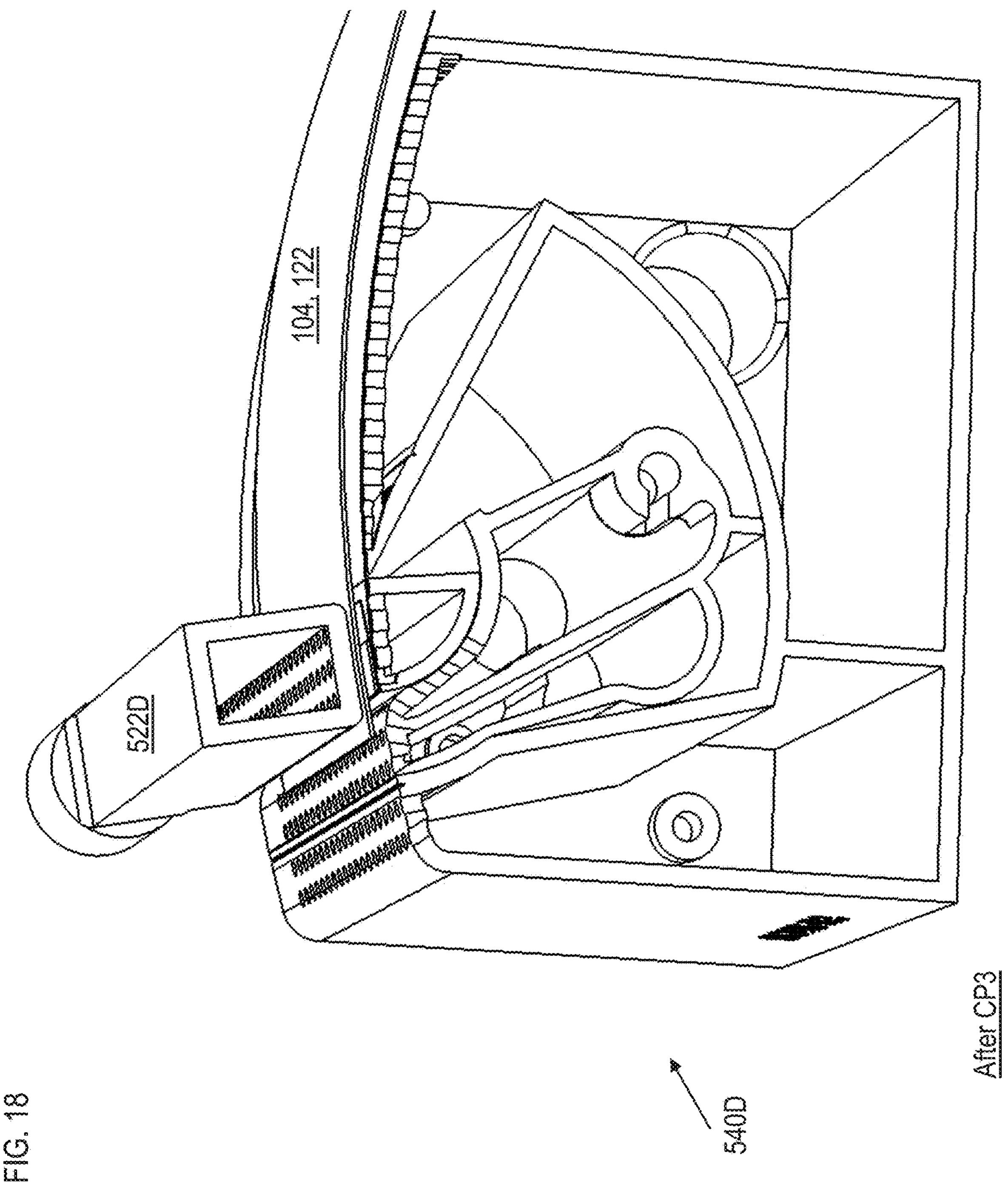
Figure 19:
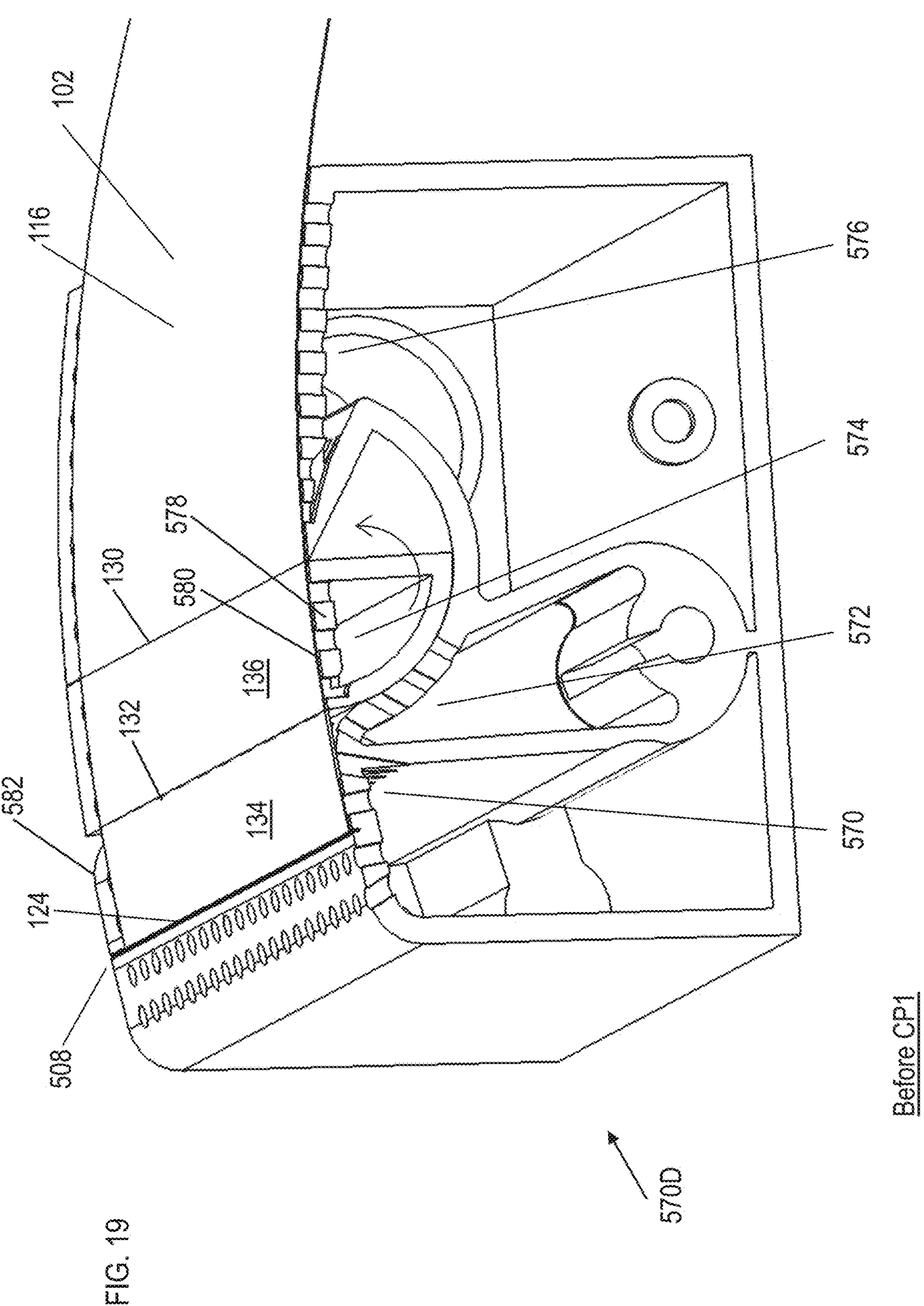
FIG. 19 to FIG. 22 are examples according to various configurations schematically illustrating views of an alternate downstream folding mechanism of the folding drum in various stages of the folding process from the operator side.

As may be seen between FIG. 16 and FIG. 17, further rotation of the folding finger 542 relative to the separation finger 544 pulls the first segment 134 through a ramp 558 that is integral to the separation finger 544 while holding the second segment to the folding finger 542. A relatively light vacuum maintains contact of the first segment 134 with the ramp 558 via vacuum holes 562 but minimizes frictional drag while a relatively stronger vacuum holds the second segment 136 to a holding surface 560 of the folding finger 542 via the vacuum holes 562. To facilitate the appropriate vacuum levels, the downstream folding mechanism 540D shown includes a separation finger vacuum zone 550, a ramp vacuum zone 552, a folding finger vacuum zone 554, and a folding assembly vacuum zone 556.

The continued rotational displacement of the folding finger 542 and the second segment 136 relative to the separation finger 544 causes the first segment 134 to hinge and fold around the second fold line 132. The first segment 134 will typically hinge around the inboard edge 114IE of the fastening component 114, thereby creating the second fold. The rotational displacement of the folding finger 542 is sufficient so that completing the second fold will allow the end of first segment 134 to clear the first surface 120 of the second belt 104. Once the folding finger 542 has been fully actuated to a maximum rotation as shown in FIG. 17, the first segment 134 will be partially folded around the second fold line 132. Positive pressure blow off air 564 is applied through ramp holes 558H in the ramp 558. The blow off air pushes the first segment 134 toward the second segment 136 until they contact, and the second fold is completed. In the completed fold, the first surface 116 of the first segment 134 is adjacent the first surface 116 of the second segment 136. Vacuum applied the vacuum holes 562 in the folding finger 542 will often bleed through the partially air permeable material of the second segment 136 and will allow the first segment 134 to be controlled by the vacuum holes 562. The fastening component 114 will often have lower air permeability than the belt material 102. Lower air permeability of the fastening component 114 improves the ability of vacuum and positive pressure blow off air to control the first segment 134.

After completion of the second fold, the fastening component 114 faces the first surface 120 of the second belt 104. The fastening component 114 with the first segment 134 and the second segment 136 are all controlled by vacuum supplied to the holding surface 560 surface of the folding finger 542. The second belt 104 is controlled by the downstream finger 522D (or by the separation belt 900 in an alternate configuration). The rotation of the folding finger 542 is reversed so that the first fold is unfolded about the first fold line 130. This displaces the fastening component 114 to move closer to the first surface 120 of the second belt 104.

The folding finger 542 continues to rotate about the first fold line 130 until the first fold is completely unfolded and the fastening component 114 comes into contact with the first surface 120 of the second belt 104. This contact causes temporary adhesion between the outer surface of the fastening component 114 and the first surface 120 of the second belt 104. The folding finger 542 may be further displaced to generate clamping pressure against the downstream finger 522D (or the separation belt 900). This applied pressure between the first belt 102 and the second belt 104 squeezes the fastening component 114. This may better bed the fastening component 114 into the first surface 120 of the second belt 104 to assure a strong temporary bond at the rescalable side scam 112. While the side seam 112 is clamped between the folding finger 542 and the downstream finger 522D, heat can be applied to the side seam 112 to enhance the temporary bond or to create a permanent bond. Heat can be supplied to the side seam 112 by hot air, ultrasonic welding, laser welding, electric resistive impulse heating, conduction, radiation, or convection. The rescalable side seam 112 created between the fastening component 114 attached to the first belt 102 and the second belt 104 is held by vacuum against the extended downstream finger 522D on the folding drum 504. Vacuum supply is reduced and shut off to the downstream finger 522D (or to the separation belt 900) and the downstream finger 522D is radially extended and axially retracted. A bonding roll 510 may be used to generate additional pressure into the rescalable side scam 112 against the folding finger 542. The folding mechanism 540D can alternatively be used to fold the first belt 102 only without the second belt 104 and without the downstream finger 522D or separation belt 900.

FIG. 19 to FIG. 22 are examples according to various configurations schematically illustrating views of an alternate configuration of the downstream folding mechanism 570D suitable for use in the folding drum 540 in various stages of the folding process from the operator side. In FIG. 19 to FIG. 22, the second belt 104 is removed to reveal the first belt 102. In the configuration shown, the downstream folding mechanism 570D works in conjunction with the downstream finger 522D (not shown in FIG. 19 to FIG. 22) like detailed for the configuration of FIG. 15 to FIG. 18. In an alternate configuration, the downstream folding mechanism 570D work in conjunction with the separation belt 900 (not shown in FIG. 19 to FIG. 22). Alternate techniques for controlling the second belt 104 such as those described above may be used in conjunction with the downstream finger 522D. In this configuration, the structure and function for the upstream folding mechanism 570U (not shown in FIG. 15 to FIG. 18) and the upstream finger 522U are a partial or complete mirror image of that shown for the downstream folding mechanism 570D and downstream finger 522D. The folding mechanism 570D can alternatively be used to fold the first belt 102 only without the second belt 104 and without the downstream finger 522D or separation belt 900.

In this alternate configuration, the first fold may be achieved using a folding finger 578 and a ramp 582 in the surface of the folding drum 504. The folding finger 578 is mechanically actuated to rotate around the first fold line 130. The second segment 136 is controlled by strong vacuum from the folding finger 578. The first segment 134 is controlled by a vacuum in the ramp 582. As the first segment 134 is rotated by the folding finger 578, the curved geometry of the ramp 582 causes first segment 134 to start to rotate around the second fold line 132, as may be seen in FIG. 20. Often in the ramp 582, the first segment 134 will pivot around the inboard edge 114IE of the fastening component 114, thereby resulting in a second fold around the second fold line 132. While the first belt 102 is folded by actuation of the folding finger 578 in the folding drum 504, the end of the second belt 104 is controlled by vacuum supplied to the downstream finger 522D (or to the separation belt 900). To facilitate the appropriate vacuum levels, the downstream folding mechanism 570D shown includes a folding assembly vacuum zone 1 570, a folding assembly vacuum zone 2 572, a folding finger vacuum zone 574, and a folding assembly vacuum zone 3 576.

Figure 20:
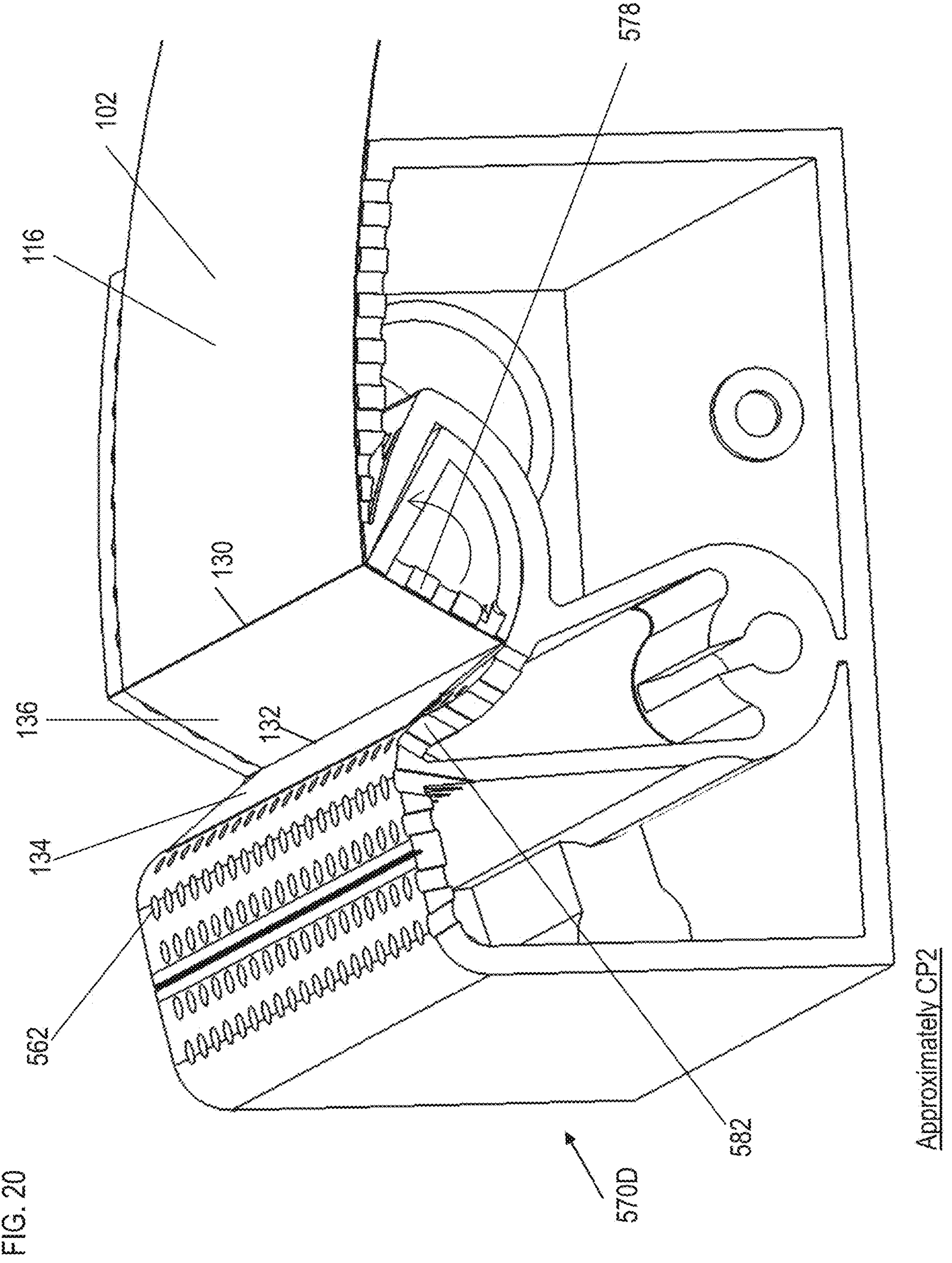
Figure 21:
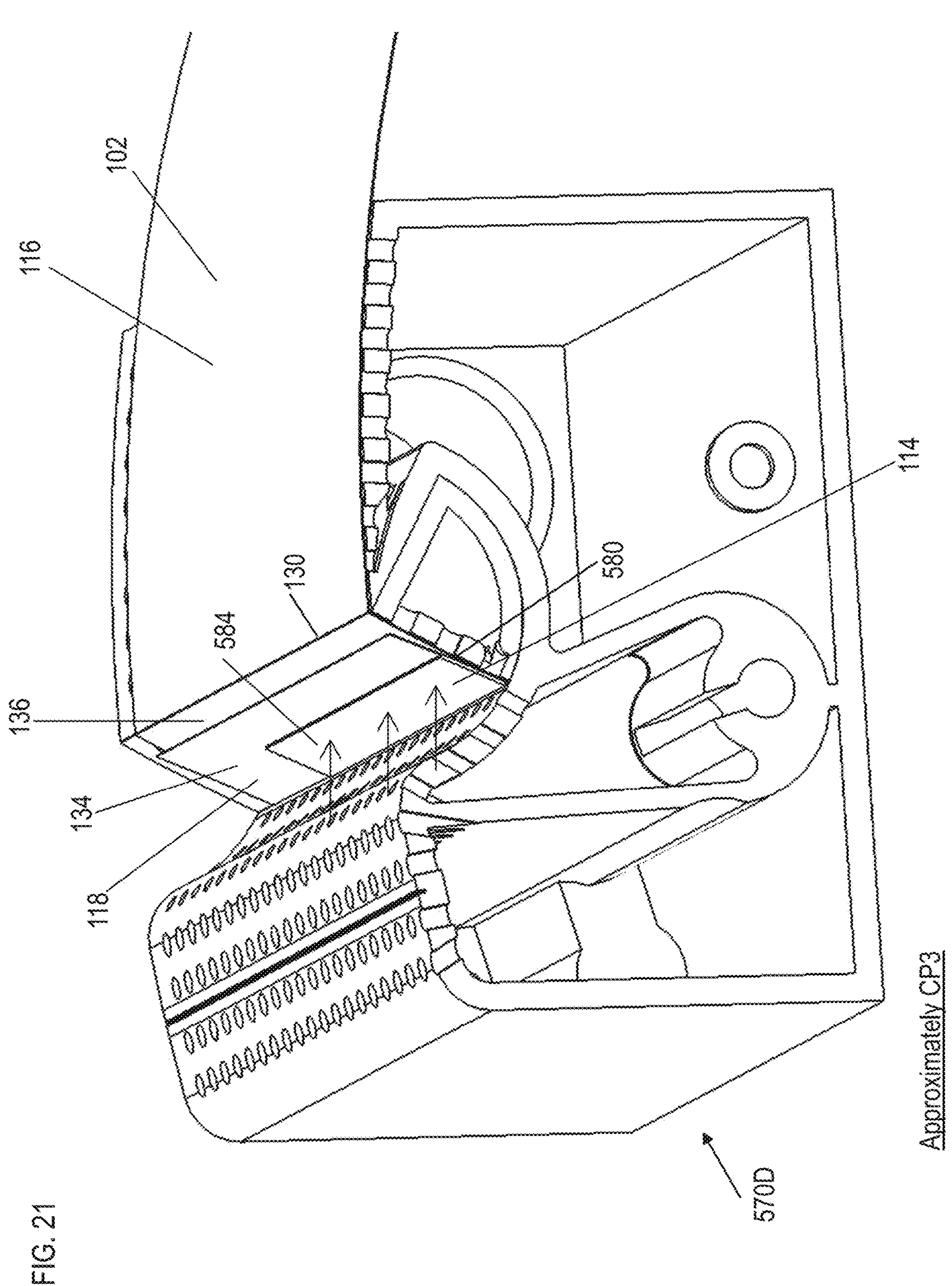
Figure 22:
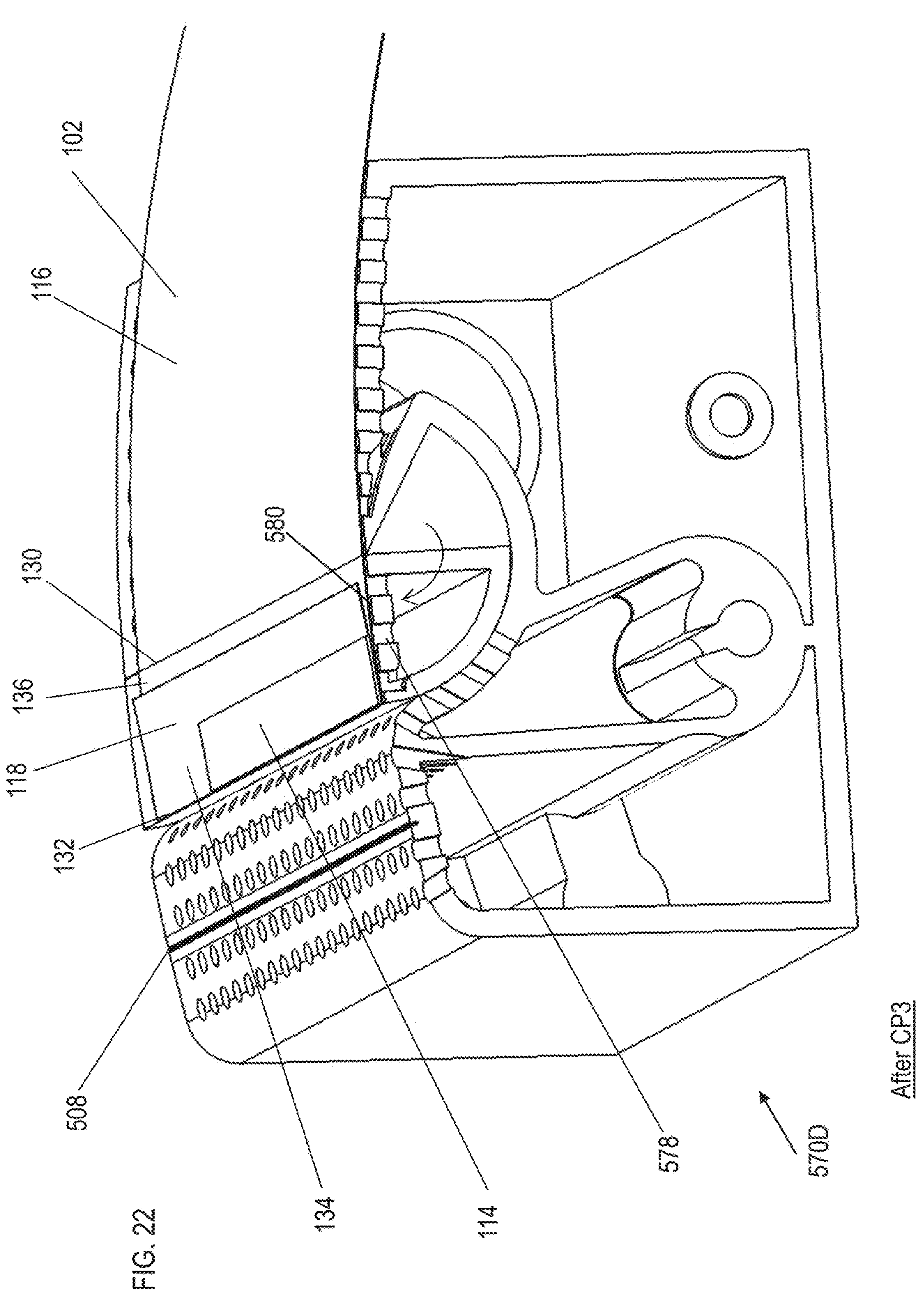

As may be seen in FIG. 20, blow off air pushes the first segment 134 toward the second segment 136 until they contact, and the second fold is completed. In the completed fold, the first surface 116 of the first segment 134 is adjacent the first surface 116 of the second segment 136. The rotation of the folding finger 578 is reversed so that the first fold is unfolded about the first fold line 130. This displaces the fastening component 114 to move closer to the first surface 120 of the second belt 104. The folding finger 578 continues to rotation about the first fold line 130 until the first fold is completely unfolded and the fastening component 114 comes into contact with the first surface 120 of the second belt 104. The folding finger 578 may be further displaced to generate clamping pressure to better bed the fastening component 114 as is detailed for FIG. 15 to FIG. 18 above.

The seamed absorbent article 100 can then be transferred from the folding drum 504 to the transfer drum 600. Vacuum may be used to control the absorbent article 100 on the transfer drum 600. Alternatively, the seamed absorbent article 100 may be transferred from the folding drum 504 to a vacuum head on a pad turner (not shown). Alternatively, the seamed absorbent article 100 may be transferred from the folding drum 504 to a vacuum conveyor (not shown).

Figures 23, 23A:
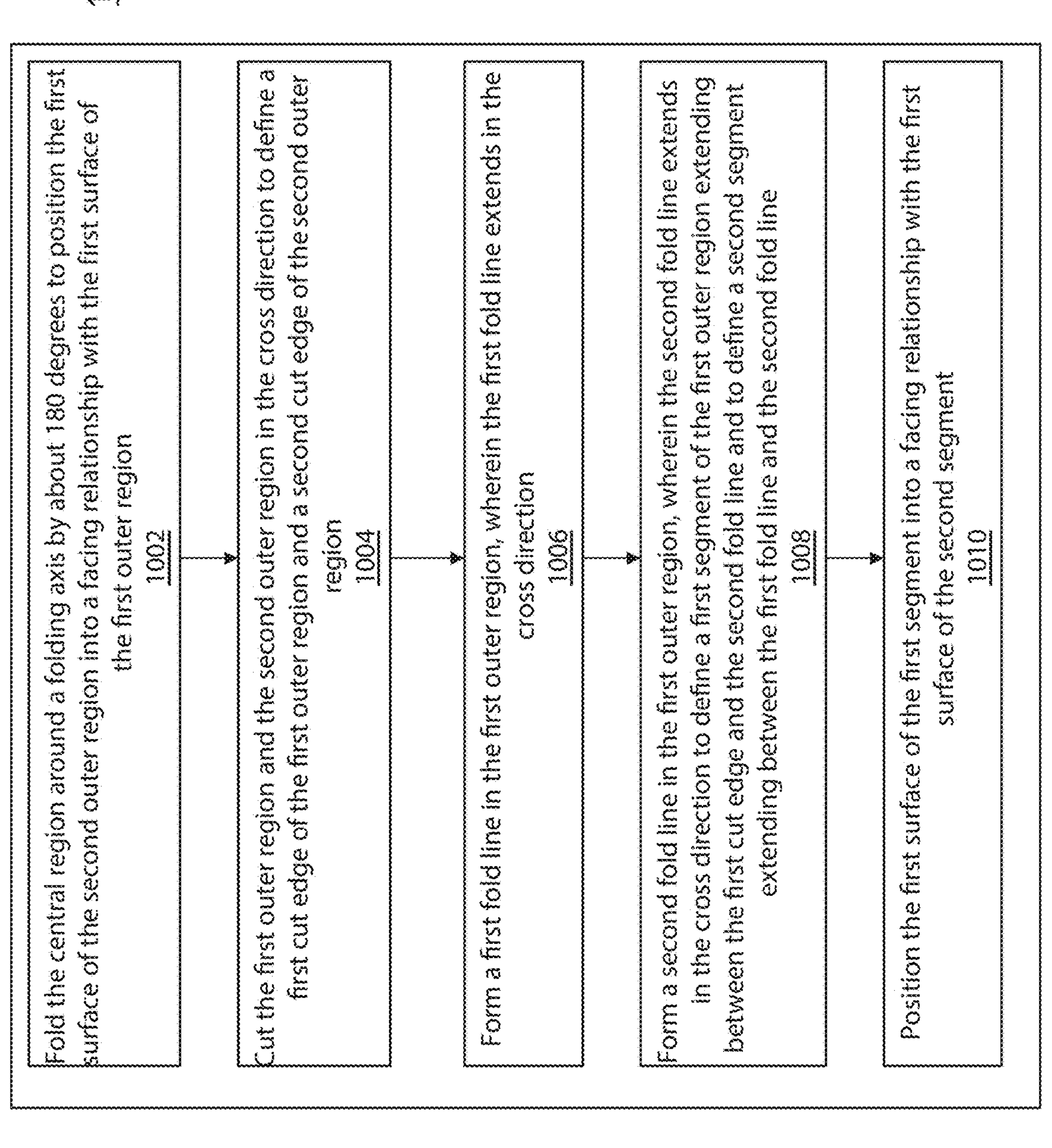
FIG. 23 is an example according to various configurations illustrating a method of folding an absorbent article.
FIG. 23A is a first partial view of FIG. 23.
Figure 23B:
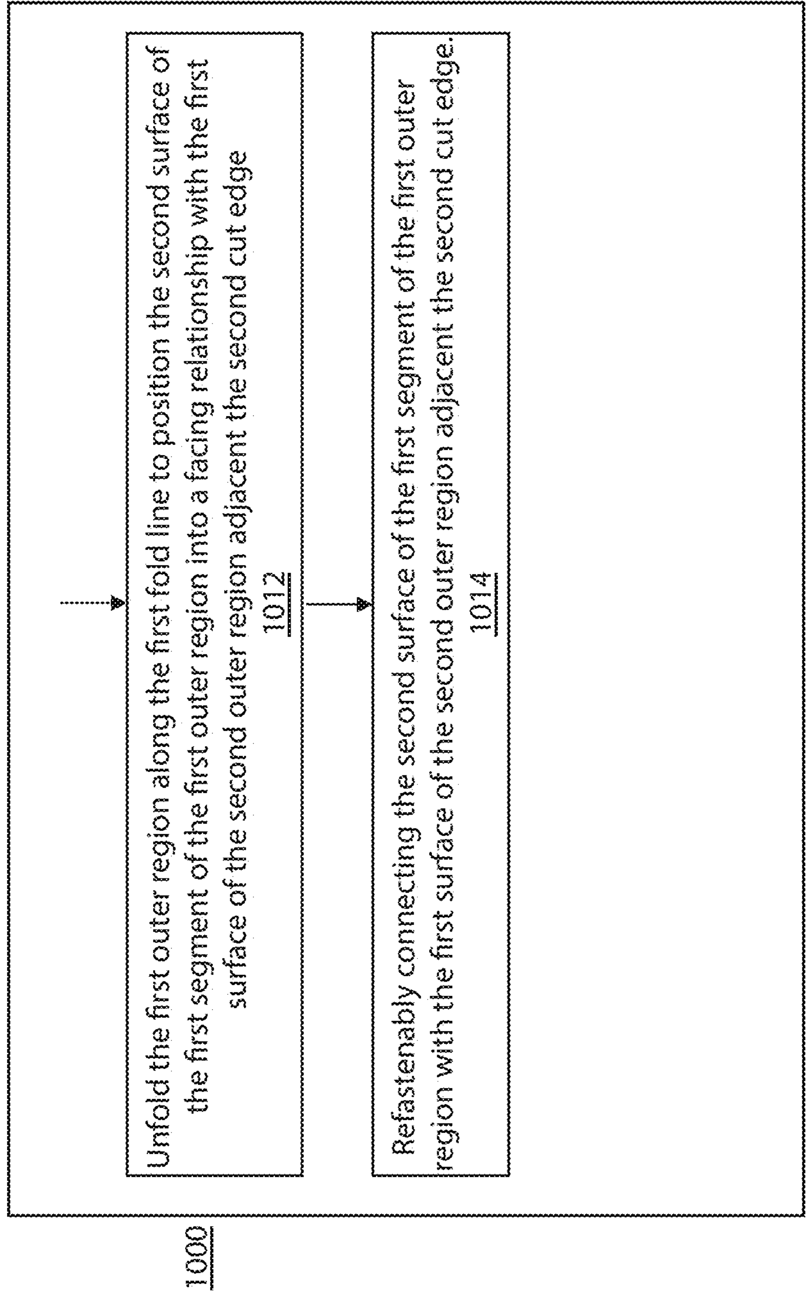
FIG. 23B is a second partial view of FIG. 23.

FIGS. 23-23B are an example according to various configurations illustrating a method 1000 of folding an absorbent article. The method includes the following steps: 1002 fold the central region around a folding axis by about 180 degrees to position the first surface of the second outer region into a facing relationship with the first surface of the first outer region; 1004 cut the first outer region and the second outer region in the cross direction to define a first cut edge of the first outer region and a second cut edge of the second outer region; 1006 form a first fold line in the first outer region, wherein the first fold line extends in the cross direction; 1008 form a second fold line in the first outer region, wherein the second fold line extends in the cross direction to define a first segment of the first outer region extending between the first cut edge and the second fold line and to define a second segment extending between the first fold line and the second fold line; 1010 position the first surface of the first segment into a facing relationship with the first surface of the second segment; 1012 unfold the first outer region along the first fold line to position the second surface of the first segment of the first outer region into a facing relationship with the first surface of the second outer region adjacent the second cut edge; and 1014 refastenably connecting the second surface of the first segment of the first outer region with the first surface of the second outer region adjacent the second cut edge.

Figures 24, 24A:
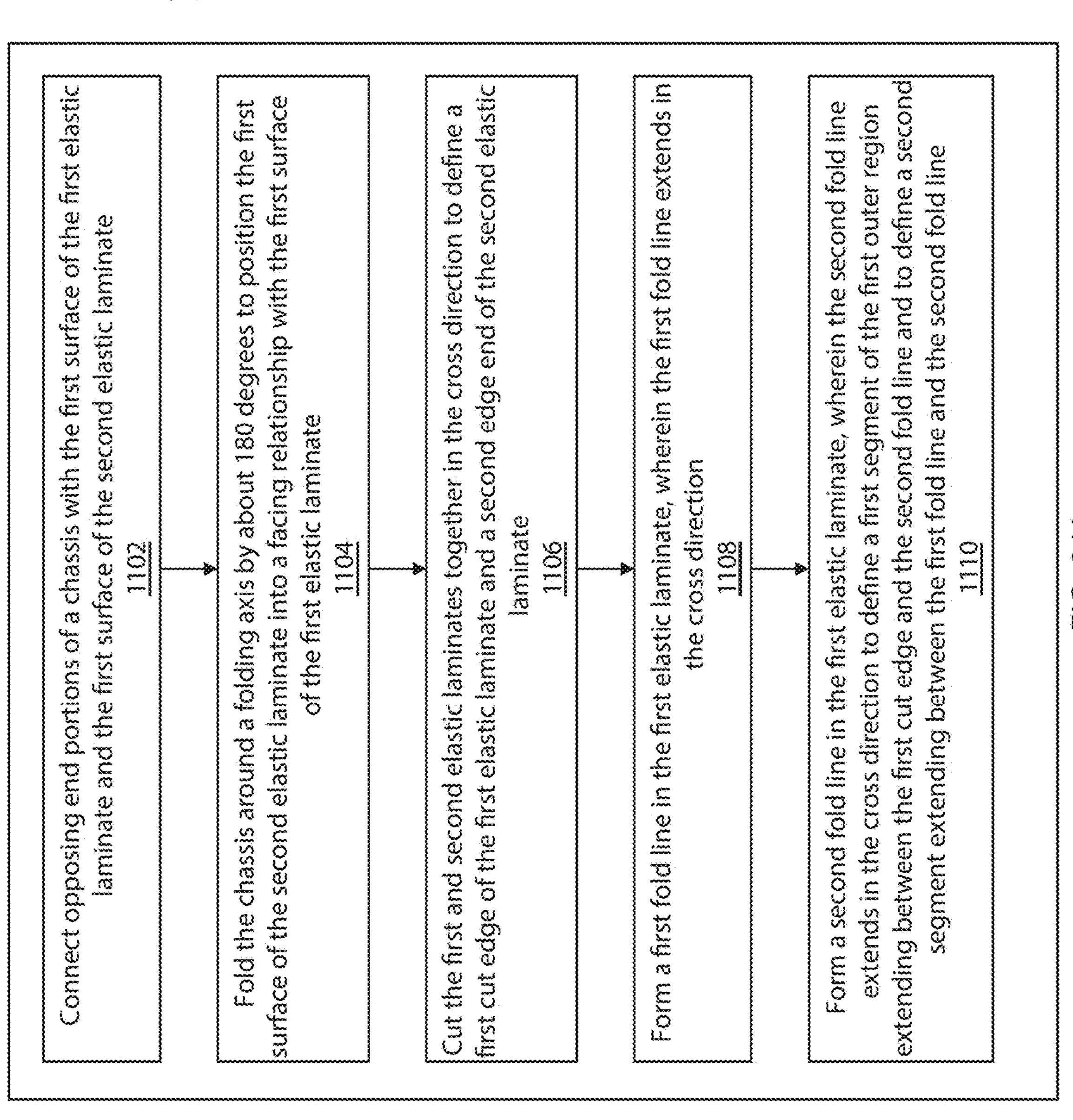
FIG. 24 is an example according to various configurations illustrating a method of folding an absorbent article.
FIG. 24A is a first partial view of FIG. 24.
Figure 24B:
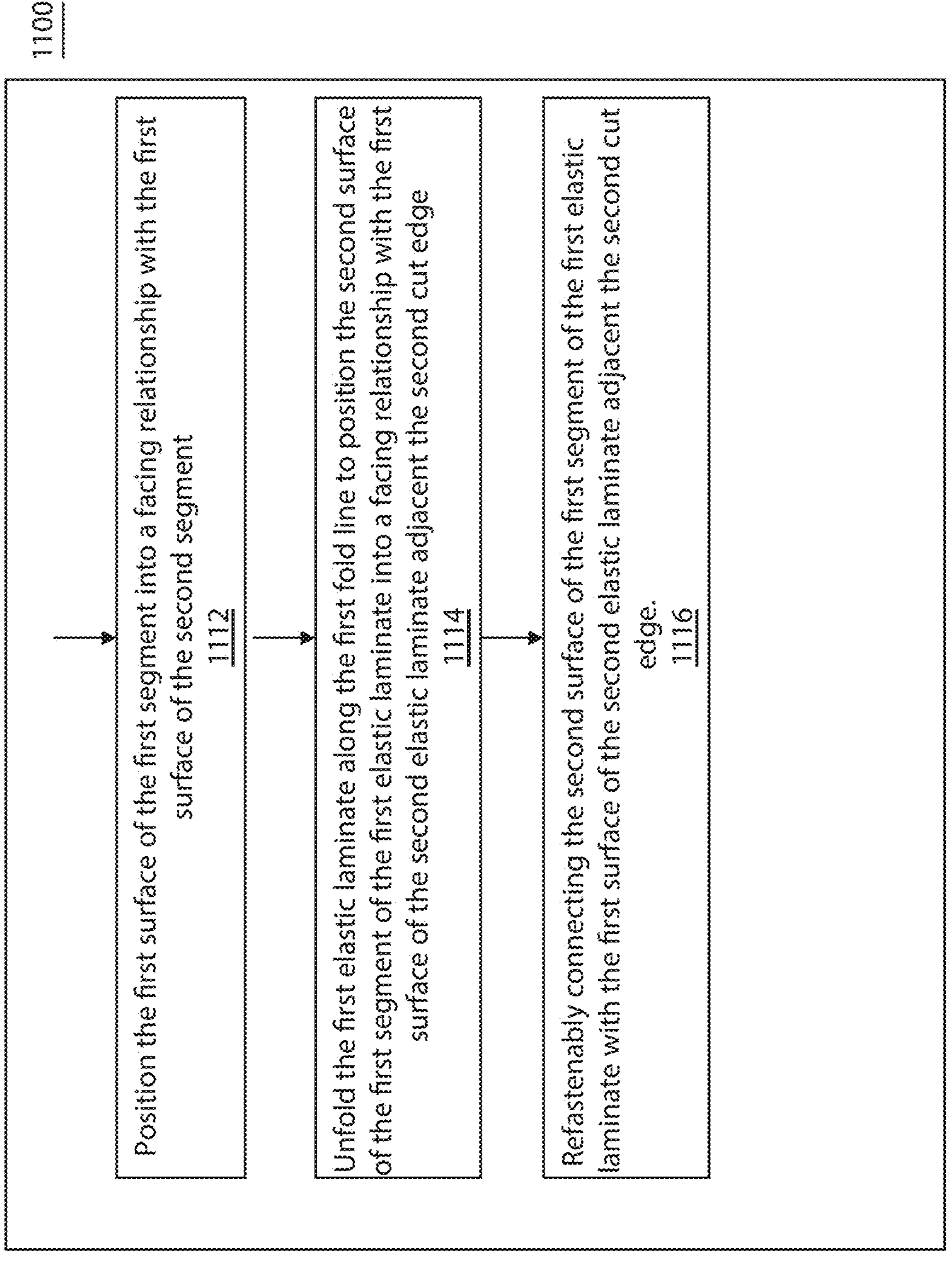
FIG. 24B is a second partial view of FIG. 24.

FIGS. 24-24B are an example according to various configurations illustrating a method 1100 of folding an absorbent article. The method includes the following steps: 1102 connect opposing end portions of a chassis with the first surface of the first elastic laminate and the first surface of the second elastic laminate; 1104 fold the chassis around a folding axis by about 180 degrees to position the first surface of the second elastic laminate into a facing relationship with the first surface of the first elastic laminate; 1106 cut the first and second elastic laminates together in the cross direction to define a first cut edge of the first elastic laminate and a second edge end of the second elastic laminate; 1108 form a first fold line in the first elastic laminate, wherein the first fold line extends in the cross direction; 1110 form a second fold line in the first elastic laminate, wherein the second fold line extends in the cross direction to define a first segment of the first outer region extending between the first cut edge and the second fold line and to define a second segment extending between the first fold line and the second fold line; 1112 position the first surface of the first segment into a facing relationship with the first surface of the second segment; 1114 unfold the first elastic laminate along the first fold line to position the second surface of the first segment of the first elastic laminate into a facing relationship with the first surface of the second elastic laminate adjacent the second cut edge; and 1116 refastenably connecting the second surface of the first segment of the first elastic laminate with the first surface of the second elastic laminate adjacent the second cut edge.

The BOHS apparatus 500 and method can also produce joined rings of overlapping belts without having a chassis 106 present. In addition, the BOHS apparatus 500 and method may be applied to a single belt, resulting in the end folded along the second fold line 132 and a section of the second surface 118 of the first belt 102 folded by the second fold. The BOHS apparatus 500 and method can also be applied to create folds in the cross machine direction CD of discrete components and discrete articles such as taped diapers, diaper cars, sanitary napkins, tissues, napkins, etc.

In addition, where two folds are created at the ends of only one belt, two folds may be created at the ends of each of the first belt 102 and the second belt 104. Alternately, one fold may be created at one end of one belt and at the opposite end of the other belt.

The methods and apparatuses disclosed above can also be used to create permanent seams between the first belt 102 and the second belt 104. Alternative means for producing permanent seams between the first belt 102 and the second belt 104 include adhesive bonding, ultrasonic welding, heat sealing, laser welding, hot air welding, crimping, compression bonding, etc.

In the absorbent article 100 disclosed herein, each belt experiences tensile stress when in use (see FIG. 1). Having an overlapping resealable side seam 112 as disclosed allows each belt to remain in tension and puts the fastening component 114 in shear stress. In other designs, the first surface 116 of the first belt 102 is connected to the first surface 120 of the second belt 102. When such a design is in use, the interface between the first belt 102 and the second belt 104 is subject to a peeling action where the belts want to peel away from each other. A fastening component 114 may be better able to withstand the sheer stress than the peeling action. Hence, methods and apparatuses that create the absorbent article 100 represent an improvement in the art.

Various Configurations with Reference to All Figures

Having described each figure individually, a non-limiting description of various configurations will now be provided, making reference to all figures simultaneously.

A system of one or more computers may be configured to perform particular operations or actions by virtue of having software, firmware, hardware, or a combination of them installed on the system that in operation causes or cause the system to perform the actions. One or more computer programs may be configured to perform particular operations or actions by virtue of including instructions that, when executed by data processing apparatus, cause the apparatus to perform the actions.

One general aspect includes a method of assembling absorbent articles 100. The method also includes advancing a substrate 140 in a machine direction MD, the substrate 140 may include a first surface 116, 120 and an opposing second surface 118, 122, the substrate 140 may include a first outer region 102 separated from a second outer region 104 in a cross direction MD by a central region 106, where the first outer region 102 and the second outer region 104 are continuous in the machine direction MD and where the central region 106 is discontinuous in the machine direction MD. The method also includes folding the central region 106 around a folding axis 128 by about 180 degrees to position the first surface 120 of the second outer region 104 into a facing relationship with the first surface 116 of the first outer region 102. The method also includes cutting the first outer region 102 and the second outer region 104 in the cross direction to define a first cut edge 124 of the first outer region 102 and a second cut edge 126 of the second outer region 104. The method also includes forming a first fold line 130 in the first outer region 102, where the first fold line 130 extends in the cross direction MD. The method also includes forming a second fold line 132 in the first outer region 102, where the second fold line 132 extends in the cross direction MD to define a first segment 134 of the first outer region 102 extending between the first cut edge 124 and the second fold line 132 and to define a second segment 136 extending between the first fold line 130 and the second fold line 132. The method also includes positioning the first surface 116 of the first segment 134 into a facing relationship with the first surface 116 of the second segment 136. The method also includes unfolding the first outer region 102 along the first fold line 130 to position the second surface 118 of the first segment 134 of the first outer region 102 into a facing relationship with the first surface 120 of the second outer region 104 adjacent the second cut edge 126. The method also includes refastenably connecting the second surface 118 of the first segment 134 of the first outer region 102 with the first surface 120 of the second outer region 104 adjacent the second cut edge 126. Other configurations of this aspect include corresponding computer systems, apparatus, and computer programs recorded on one or more computer storage devices, each configured to perform the actions of the methods.

Implementations may include one or more of the following features. The method where the step of forming the first fold line 130 is performed before the step of forming the second fold line 132. The step of forming the first fold line 130 and the step of forming the second fold line 132 are performed simultaneously. The method of any to 3, may include a step of bonding a first fastening component 114 onto the second surface 118 of the first outer region 102. The first fastening component 114 is positioned on the first segment 134. The first outer region 102 and the second outer region 104 are elastically contractible in the machine direction MD. The method may include a step of elastically contracting a portion of the second outer region 104 in the machine direction MD adjacent the second cut edge 126. The central region 106 may include a chassis 106 may include a topsheet 106*t* and a backsheet 106*b* and absorbent assembly 106*a* positioned between the topsheet 106*t* and the backsheet 106*b*. The first fastening component 114 may include hooks or loops. Implementations of the described techniques may include hardware, a method or process, or computer software on a computer-accessible medium.

One general aspect includes a method of assembling absorbent articles 100. The method also includes advancing a first elastic laminate 102 in a machine direction MD, the first elastic laminate 102 may include a first surface 116 and an opposing second surface 118. The method also includes advancing a second elastic laminate 104 in the machine direction MD, the second elastic laminate 104 may include a first surface 120 and an opposing second surface 122, the second elastic laminate 104 separated from the first elastic laminate 102 in a cross direction MD. The method also includes connecting opposing end portions of a chassis 106 with the first surface 116 of the first elastic laminate 102 and the first surface 120 of the second elastic laminate 104. The method also includes folding the chassis 106 around a folding axis by about 180 degrees to position the first surface 120 of the second elastic laminate 104 into a facing relationship with the first surface 116 of the first elastic laminate 102. The method also includes cutting the first 102 and second elastic laminates 104 together in the cross direction MD to define a first cut edge 124 of the first elastic laminate 102 and a second cut edge 126 of the second elastic laminate 104. The method also includes forming a first fold line 130 in the first elastic laminate 102, where the first fold line 130 extends in the cross direction MD. The method also includes forming a second fold line 132 in the first elastic laminate 102, where the second fold line 132 extends in the cross direction MD to define a first segment 134 of the first outer region 102 extending between the first cut edge 124 and the second fold line 132 and to define a second segment 136 extending between the first fold line 130 and the second fold line 132. The method also includes positioning the first surface 116 of the first segment 134 into a facing relationship with the first surface 116 of the second segment 136. The method also includes unfolding the first elastic laminate 102 along the first fold line 130 to position the second surface 118 of the first segment 134 of the first elastic laminate 102 into a facing relationship with the first surface 120 of the second elastic laminate 104 adjacent the second cut edge 126. The method also includes refastenably connecting the second surface 118 of the first segment 134 of the first elastic laminate 102 with the first surface 120 of the second elastic laminate 104 adjacent the second cut edge 126. Other configurations of this aspect include corresponding computer systems, apparatus, and computer programs recorded on one or more computer storage devices, each configured to perform the actions of the methods.

Implementations may include one or more of the following features. The method may include a step of bonding a first fastening component 114 onto the second surface 118 of the first elastic laminate 102. The first fastening component 114 is positioned on the first segment 134. The method of any to 13, may include a step of advancing the first 102 and second elastic laminates 104 onto a rotating drum 504 subsequent to the step of folding the chassis 106, such the first elastic laminate 102 is positioned between the second elastic laminate 104 and the drum 504. The method may include a step of applying a vacuum pressure to a portion 134, 136 of the first elastic laminate 102 with a holding surface 560, 580 of a folding member 542, 578 that is pivotally connected with drum 504. The steps of forming the first fold line 130 and the second fold line 132 further may include pivoting the folding member 542, 578 in a first direction to move the holding surface 560, 580 and the portion 134, 136 of the first elastic laminate 102 away from the second elastic laminate 104. The step of positioning the first surface 116 of the first segment 134 into a facing relationship with the first surface 116 of the second segment 136 further may include applying positive air pressure 584 against the second surface 118 of the first segment 134. The step of unfolding the first elastic laminate 102 along the first fold line 130 further may include pivoting the folding member 542, 578 in a second direction opposite the first direction. The step of forming the first fold line 130 is performed before the step of forming the second fold line 132. The step of forming the first fold line 130 and the step of forming the second fold line 132 are performed simultaneously. The step of cutting further may include cutting the first fastening component 114 into an upstream fastening component 114*u* and a downstream fastening component 114*d*. Implementations of the described techniques may include hardware, a method or process, or computer software on a computer-accessible medium.

One general aspect includes an apparatus 500 for forming a refastenable connection 112 between a first elastic laminate 102 and a second elastic laminate 104. The apparatus also includes a drum 504 adapted to rotate about an axis 504*a*, the drum 504 may include an outer circumferential surface 504*c*; a folding mechanism 540*u*, 540*d* adjacent the outer circumferential surface 504*c*, the folding mechanism 540*u*, 540*d* may include a first folding member 540*u* may include a first holding surface 560, 580 and a second folding member 540*d* may include a second holding surface 560, 580, the first folding member 540*u* and the second folding member 540*d* pivotally connected with the drum 504 and pivotal between a first position and a second position, where the first holding surface 560, 580 and the second holding surface 560, 580 are generally aligned with the outer circumferential surface 504*c* of the drum 504 in the first position, and where the first holding surface 560, 580 and the second holding surface 560, 580 are retracted radially inward from the outer circumferential surface 504*c* of the drum 504 in the second position; and an anvil 508 positioned circumferentially between the first folding member 540*u* and the second folding member 540*d*. Other configurations of this aspect include corresponding computer systems, apparatus, and computer programs recorded on one or more computer storage devices, each configured to perform the actions of the methods.

Combinations

A1. A method of assembling absorbent articles, the method comprising steps of: advancing a substrate in a machine direction, the substrate comprising a first surface and an opposing second surface, the substrate further comprising a first outer region separated from a second outer region in a cross direction by a central region, wherein the first outer region and the second outer region are continuous in the machine direction and wherein the central region is discontinuous in the machine direction; folding the central region around a folding axis by about 180 degrees to position the first surface of the second outer region into a facing relationship with the first surface of the first outer region; cutting the first outer region and the second outer region in the cross direction to define a first cut edge of the first outer region and a second cut edge of the second outer region; forming a first fold line in the first outer region, wherein the first fold line extends in the cross direction; forming a second fold line in the first outer region, wherein the second fold line extends in the cross direction to define a first segment of the first outer region extending between the first cut edge and the second fold line and to define a second segment extending between the first fold line and the second fold line; positioning the first surface of the first segment into a facing relationship with the first surface of the second segment; unfolding the first outer region along the first fold line to position the second surface of the first segment of the first outer region into a facing relationship with the first surface of the second outer region adjacent the second cut edge; and refastenably connecting the second surface of the first segment of the first outer region with the first surface of the second outer region adjacent the second cut edge.

A2. The method of paragraph A1, wherein the step of forming the first fold line is performed before the step of forming the second fold line.

A3. The method of paragraph A1, wherein the step of forming the first fold line and the step of forming the second fold line are performed simultaneously.

A4. The method of any of paragraphs A1-A3, further comprising a step of bonding a first fastening component onto the second surface of the first outer region.

A5. The method of paragraph A4, wherein the first fastening component is positioned on the first segment.

A6. The method of paragraph A4, wherein the first fastening component comprises hooks or loops.

A7. The method of any of paragraphs A1-A6, wherein the first outer region and the second outer region are elastically contractible in the machine direction.

A8. The method of paragraph A7, further comprising a step of elastically contracting a portion of the second outer region in the machine direction adjacent the second cut edge.

A9. The method of paragraph A1, wherein the central region comprises a chassis comprising a topsheet and a backsheet and absorbent assembly positioned between the topsheet and the backsheet.

B1. A method of assembling absorbent articles, the method comprising steps of: advancing a first clastic laminate in a machine direction, the first elastic laminate comprising a first surface and an opposing second surface; advancing a second elastic laminate in the machine direction, the second elastic laminate comprising a first surface and an opposing second surface, the second elastic laminate separated from the first elastic laminate in a cross direction; connecting opposing end portions of a chassis with the first surface of the first elastic laminate and the first surface of the second elastic laminate; folding the chassis around a folding axis by about 180 degrees to position the first surface of the second elastic laminate into a facing relationship with the first surface of the first elastic laminate; cutting the first and second elastic laminates together in the cross direction to define a first cut edge of the first elastic laminate and a second cut edge of the second elastic laminate; forming a first fold line in the first elastic laminate, wherein the first fold line extends in the cross direction; forming a second fold line in the first elastic laminate, wherein the second fold line extends in the cross direction to define a first segment of the first outer region extending between the first cut edge and the second fold line and to define a second segment extending between the first fold line and the second fold line; positioning the first surface of the first segment into a facing relationship with the first surface of the second segment; unfolding the first elastic laminate along the first fold line to position the second surface of the first segment of the first elastic laminate into a facing relationship with the first surface of the second elastic laminate adjacent the second cut edge; and refastenably connecting the second surface of the first segment of the first elastic laminate with the first surface of the second elastic laminate adjacent the second cut edge.

B2. The method of paragraph B1, further comprising a step of bonding a first fastening component onto the second surface of the first elastic laminate.

B3. The method of paragraph B2, wherein the first fastening component is positioned on the first segment.

B4. The method of paragraph B2, wherein the step of cutting further comprises cutting the first fastening component into an upstream fastening component and a downstream fastening component.

B5. The method of any of paragraphs B1-B4, further comprising a step of advancing the first and second clastic laminates onto a rotating drum subsequent to the step of folding the chassis, such the first elastic laminate is positioned between the second elastic laminate and the drum.

B6. The method of paragraph B5, further comprising a step of applying a vacuum pressure to a portion of the first elastic laminate with a holding surface of a folding member that is pivotally connected with drum.

B7. The method of paragraph B6, wherein the steps of forming the first fold line and the second fold line further comprise pivoting the folding member in a first direction to move the holding surface and the portion of the first elastic laminate away from the second elastic laminate.

B8. The method of paragraph B7, wherein the step of positioning the first surface of the first segment into a facing relationship with the first surface of the second segment further comprises applying positive air pressure against the second surface of the first segment.

B9. The method of paragraph B8, wherein the step of unfolding the first elastic laminate along the first fold line further comprises pivoting the folding member in a second direction opposite the first direction.

B10. The method of any of paragraphs B1-B9, wherein the step of forming the first fold line is performed before the step of forming the second fold line.

B11. The method of any of paragraphs B1-B9, wherein the step of forming the first fold line and the step of forming the second fold line are performed simultaneously.

Bio-Based Content for Components

Components of the absorbent articles described herein may at least partially be comprised of bio-based content as described in U.S. Pat. Appl. Pub. No. 2007/0219521 A1. For example, the superabsorbent polymer component may be bio-based via their derivation from bio-based acrylic acid. Bio-based acrylic acid and methods of production are further described in U.S. Pat. Appl. Pub. No. 2007/0219521 and U.S. Pat. Nos. 8,703,450; 9,630,901 and 9,822,197. Other components, for example nonwoven and film components, may comprise bio-based polyolefin materials. Bio-based polyolefins are further discussed in U.S. Pat. Appl. Pub. Nos. 2011/0139657, 2011/0139658, 2011/0152812, and 2016/

0206774, and U.S. Pat. No. 9,169,366. Example bio-based polyolefins for use in the present disclosure comprise polymers available under the designations SHA7260™, SHE150™, or SGM9450F™ (all available from Braskem S.A.).

An absorbent article component may comprise a bio-based content value from about 10% to about 100%, from about 25% to about 100%, from about 40% to about 100%, from about 50% to about 100%, from about 75% to about 100%, or from about 90% to about 100%, for example, using ASTM D6866-10, method B.

Recycle Friendly and Bio-Based Absorbent Articles

Components of the absorbent articles described herein may be recycled for other uses, whether they are formed, at least in part, from recyclable materials. Examples of absorbent article materials that may be recycled are nonwovens, films, fluff pulp, and superabsorbent polymers. The recycling process may use an autoclave for sterilizing the absorbent articles, after which the absorbent articles may be shredded and separated into different byproduct streams. Example byproduct streams may comprise plastic, superabsorbent polymer, and cellulose fiber, such as pulp. These byproduct streams may be used in the production of fertilizers, plastic articles of manufacture, paper products, viscose, construction materials, absorbent pads for pets or on hospital beds, and/or for other uses. Further details regarding absorbent articles that aid in recycling, designs of recycle friendly diapers, and designs of recycle friendly and bio-based component diapers, are disclosed in U.S. Pat. Appl. Publ. No. 2019/0192723, published on Jun. 27, 2019.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular configurations of the present disclosure have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method of assembling absorbent articles, the method comprising steps of:

advancing a substrate in a machine direction, the substrate comprising a first surface and an opposing second surface, the substrate further comprising a first outer region separated from a second outer region in a cross direction by a central region, wherein the first outer region and the second outer region are continuous in the machine direction, wherein the central region is discontinuous in the machine direction, wherein the first outer region comprises a first portion of the first surface, and wherein the second outer region comprises a second portion of the first surface;

folding the central region around a folding axis by about 180 degrees to position the second portion of the first surface into a facing relationship with the first portion of the first surface;

cutting the first outer region and the second outer region in the cross direction to define a first cut edge of the first outer region and a second cut edge of the second outer region;

forming a first fold line in the first outer region, wherein the first fold line extends in the cross direction;

forming a second fold line in the first outer region, wherein the second fold line extends in the cross direction to define a first segment of the first outer region extending between the first cut edge and the second fold line and to define a second segment extending between the first fold line and the second fold line, wherein the first segment of the first outer region comprises a third portion of the first surface and a first portion of the second surface, and wherein the second segment comprises a fourth portion of the first surface;

positioning the third portion of the first surface into a facing relationship with the fourth portion of the first surface;

unfolding the first outer region along the first fold line to position the first portion of the second surface into a facing relationship with the second portion of the first surface adjacent the second cut edge; and refastenably connecting the first portion of the second surface with the second portion of the first surface adjacent the second cut edge.

2. The method of claim 1, wherein the step of forming the first fold line is performed before the step of forming the second fold line.

3. The method of claim 2, further comprising a step of bonding a first fastening component onto a second portion of the second surface, wherein the first outer region comprises the second portion of the second surface.

4. The method of claim 1, wherein the step of forming the first fold line and the step of forming the second fold line are performed simultaneously.

5. The method of claim 1, further comprising a step of bonding a first fastening component onto a second portion of the second surface, wherein the first outer region comprises the second portion of the second surface.

6. The method of claim 5, wherein the first fastening component is positioned on the first segment.

7. The method of claim 5, wherein the first fastening component comprises hooks or loops.

8. The method of claim 5, wherein the first fastening component comprises contact adhesive.

9. The method of claim 5, wherein the first fastening component comprises co-adhesive coatings.

10. The method of claim 5, wherein the first fastening component comprises interlocking mechanical fasteners.

11. The method of claim 5, wherein the first fastening component comprises magnetic closures.

12. The method of claim 5, wherein the first fastening component comprises snaps.

13. The method of claim 5, wherein the step of cutting further comprises cutting the first fastening component into an upstream fastening component and a downstream fastening component.

14. The method of claim 1, wherein the first outer region and the second outer region are elastically contractible in the machine direction.

15. The method of claim 14, further comprising a step of elastically contracting a portion of the second outer region in the machine direction adjacent the second cut edge.

16. The method of claim 1, wherein the central region comprises a chassis comprising a topsheet and a backsheet and an absorbent assembly positioned between the topsheet and the backsheet.

17. The method of claim 1, further comprising a step of advancing the first outer region and the second outer region onto a rotating drum subsequent to the step of folding the central region, such that the first outer region is positioned between the second outer region and the drum.

18. The method of claim 17, further comprising a step of applying a vacuum pressure to a portion of the first outer region with a holding surface of a folding member that is pivotally connected with the drum.

19. The method of claim 18, wherein the steps of forming the first fold line and the second fold line further comprise pivoting the folding member in a first direction to move the holding surface and the portion of the first outer region away from the second outer region.

20. The method of claim 19, wherein the step of positioning the third portion of the first surface into a facing relationship with the fourth portion of the first surface further comprises applying positive air pressure against the first portion of the second surface.

21. The method of claim 20, wherein the step of unfolding the first outer region along the first fold line further comprises pivoting the folding member in a second direction opposite the first direction.

* * * * *